United States Patent
Paris et al.

(10) Patent No.: US 9,955,918 B2
(45) Date of Patent: May 1, 2018

(54) MOUTH GUARD FOR DETERMINING PHYSIOLOGICAL CONDITIONS OF A SUBJECT AND SYSTEMS AND METHODS FOR USING SAME

(71) Applicant: University of Alaska Anchorage, Anchorage, AK (US)

(72) Inventors: Anthony J. Paris, Anchorage, AK (US); Jennifer M. Brock, Anchorage, AK (US); John A. Lund, Bellingham, WA (US)

(73) Assignee: University of Alaska Anchorage, Anchorage, AK (US)

( * ) Notice: Subject to any disclaimer, the term of this patent is extended or adjusted under 35 U.S.C. 154(b) by 199 days.

(21) Appl. No.: 14/144,907

(22) Filed: Dec. 31, 2013

(65) Prior Publication Data

US 2014/0187875 A1 Jul. 3, 2014

Related U.S. Application Data

(60) Provisional application No. 61/747,411, filed on Dec. 31, 2012, provisional application No. 61/827,996, filed on May 28, 2013.

(51) Int. Cl.
| | |
|---|---|
| *A61B 5/00* | (2006.01) |
| *A61B 5/11* | (2006.01) |
| *A61B 5/0205* | (2006.01) |
| *A61B 5/01* | (2006.01) |

(52) U.S. Cl.
CPC ............ *A61B 5/6803* (2013.01); *A61B 5/01* (2013.01); *A61B 5/02055* (2013.01); *A61B 5/1121* (2013.01); *A61B 5/1126* (2013.01); *A61B 5/682* (2013.01); *A61B 5/7282* (2013.01); *A61B 5/742* (2013.01); *A61B 5/746* (2013.01); *A61B 5/7445* (2013.01); *A61B 2503/10* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 6,941,952 B1 | 9/2005 | Rush, III | |
| 7,526,389 B2 | 4/2009 | Greenwald | ............ 702/55 |
| 2004/0242976 A1* | 12/2004 | Abreu | ......... A61B 5/0008 600/315 |
| 2005/0203431 A1* | 9/2005 | Brodnick | ........... A61B 5/0809 600/529 |
| 2009/0220921 A1 | 9/2009 | Abolfathi | ............ 381/326 |
| 2011/0060237 A1* | 3/2011 | Kurosawa | ........... A61B 5/085 600/533 |

(Continued)

OTHER PUBLICATIONS

Roveti, D., Choosing a Humidity Sensor: A Review of Three Technologies, Sensors, Jul. 1, 2001.*

(Continued)

*Primary Examiner* — William Thomson
*Assistant Examiner* — Qingjun Kong
(74) *Attorney, Agent, or Firm* — Ballard Spahr LLP

(57) ABSTRACT

Mouth guards having electrodes, sensors, and/or accelerometers for determining one or more physiological conditions of a subject. Processing circuitry receives the outputs of the electrodes, sensors, and/or accelerometers. Optionally, at least a portion of the processing circuitry can be positioned within a helmet that is worn by a subject. The mouth guard can optionally be tethered to the helmet.

20 Claims, 12 Drawing Sheets

(56) References Cited

U.S. PATENT DOCUMENTS

| | | | |
|---|---|---|---|
| 2011/0219852 A1 | 9/2011 | Kasten | |
| 2013/0211270 A1* | 8/2013 | St. Laurent | A61B 5/682 600/508 |
| 2013/0245483 A1* | 9/2013 | Eichler | A61B 5/082 600/532 |
| 2014/0188010 A1 | 7/2014 | Paris | 600/595 |
| 2015/0143526 A1 | 5/2015 | Jeon et al. | |

OTHER PUBLICATIONS

Cernak, NeuroRx.: The Journal of the American Society for Experimental NeuroTherapeutics, Jul. 2005; 2(3): 410-422.*

Non-Final Office Action dated Aug. 12, 2016, for U.S. Appl. No. 14/144,791, filed Dec. 31, 2013, and published as US-2014-0188010-A1 on Jul. 3, 2014 (Applicant—University of Alaska // Inventor—Paris, et al.) (28 pages).

Paris et al., (2008) "Soccer Ball Heading Model," Proceedings of the ASME 2008 Summer Bioengineering Conference, Jun. 25-29, Marriott Resort, Marco Island, FL, USA.

Paris et al., (2010) "Accelerations of the Head During Soccer Ball Heading," Proceedings of the ASME 2010 Summer Bioengineering Conference, Jun. 16-19, Grand Beach Resort, Naples, FL, USA.

Kara et al., (2012) "Evaluation of an Instrumented Mouthguard to Measure the Accelerations of the Head due to Soccer Ball Heading," 12th Pan-American Congress of Applied Mechanics, Jan. 2-6, Port of Spain, Trinidad.

Birmingham et al., (2013) "An Instrumented Mouthguard to Measure Head Accelerations due to Impact," Proceedings of the ASME 2013 Summer Bioengineering Conference, Jun. 26-29, Sunriver, OR, USA.

Non-Final Office Action dated Mar. 23, 2017, for U.S. Appl. No. 14/144,791, filed Dec. 31, 2013, and published as US 2014/0188010 A1 on Jul. 3, 2014 (Applicant—University of Alaska // Inventor—Paris, et al.) (22 pages).

* cited by examiner

MOUTH GUARD FOR DETERMINING PHYSIOLOGICAL CONDITIONS OF A SUBJECT AND SYSTEMS AND METHODS FOR USING SAME

CROSS-REFERENCE TO RELATED APPLICATIONS

This application claims the benefit of the filing date of U.S. Provisional Patent Application No. 61/747,411, filed Dec. 31, 2012, and of U.S. Provisional Patent Application No. 61/827,996, filed May 28, 2013, both of which are hereby incorporated by reference herein in their entirety.

FIELD

This application relates to devices, systems, and methods for measuring and/or determining one or more physiological conditions of a subject.

BACKGROUND

A variety of health risks are associated with recreational and occupational activities. To identify and mitigate many of these risks, it is necessary to monitor the body to identify unusual deviations from normal body function and conditioning. However, measurements of bodily function and conditioning are generally too intrusive to be incorporated into conventional sports and occupational equipment.

Accordingly, there is a need in the pertinent art for devices, systems, and methods for measuring physiological conditions of a subject in a non-intrusive manner.

SUMMARY

Described herein is a measurement system for determining at least one physiological condition of a subject. The measurement system can include a mouth guard and processing circuitry. The mouth guard can include a U-shaped element having an outer side wall, an inner side wall, and at least one biting surface. The outer side wall, the inner side wall, and the at least one biting surface can cooperate to define at least one channel configured to receive the upper teeth of the subject. Optionally, the mouth guard can also include a plurality of electrodes operatively associated with the U-shaped element and positioned in operative communication with processing circuitry. The plurality of electrodes can be spaced from one another about the U-shaped element. The processing circuitry can be configured to measure the impedance between respective electrodes of the plurality of electrodes, and the measured impedance between the respective electrodes can be indicative of the at least one physiological condition of the subject. Optionally, the mouth guard can include accelerometers and other sensors for measuring linear and angular acceleration and various physiological parameters of the subject. One exemplary system can include a helmet, with the mouth guard being operatively coupled to the helmet by a strap or other tethering means. Methods of using the disclosed mouth guards and measurement systems are also described.

BRIEF DESCRIPTION OF THE DRAWINGS

These and other features of the preferred embodiments of the invention will become more apparent in the detailed description in which reference is made to the appended drawings wherein.

DETAILED DESCRIPTION

Figure 1:
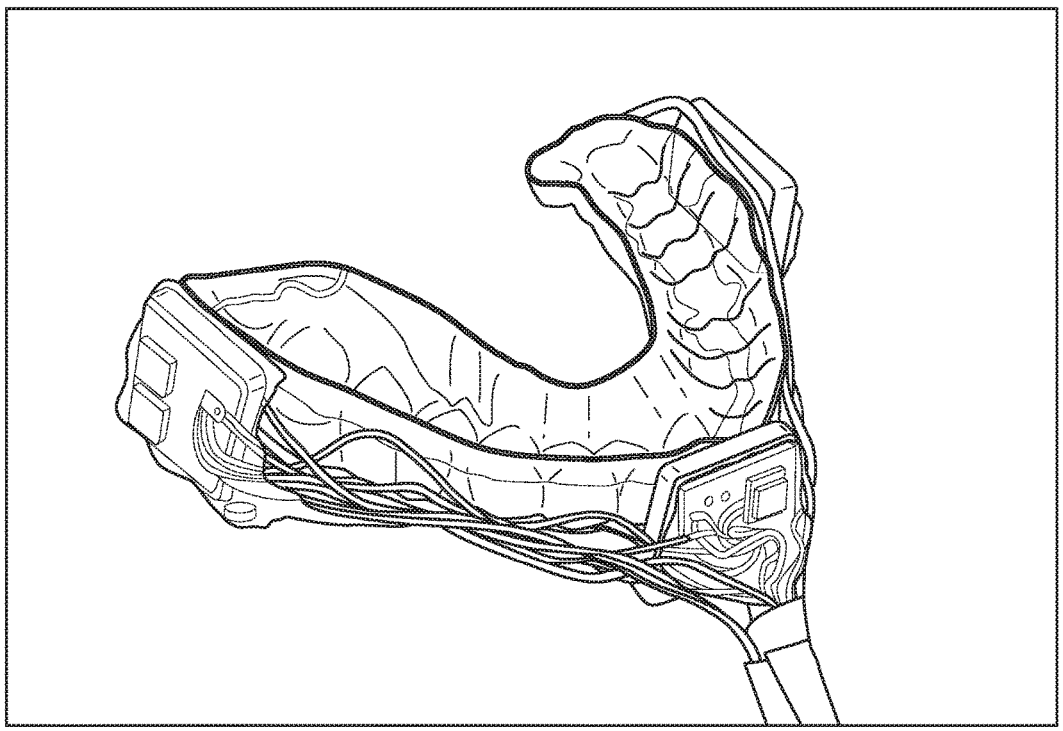
FIG. 1 is an image of an exemplary mouth guard as disclosed herein.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "an accelerometer" can include two or more such accelerometers unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

Described herein, with reference to FIGS. 1-7 and 13-15, are a mouth guard and related measurement systems and methods for determining at least one physiological condition of a subject. It is contemplated that the subject can be a human or non-human subject. It is further contemplated that the subject can have a head, a mouth, and upper and lower teeth.

The Mouth Guard

Figure 2:
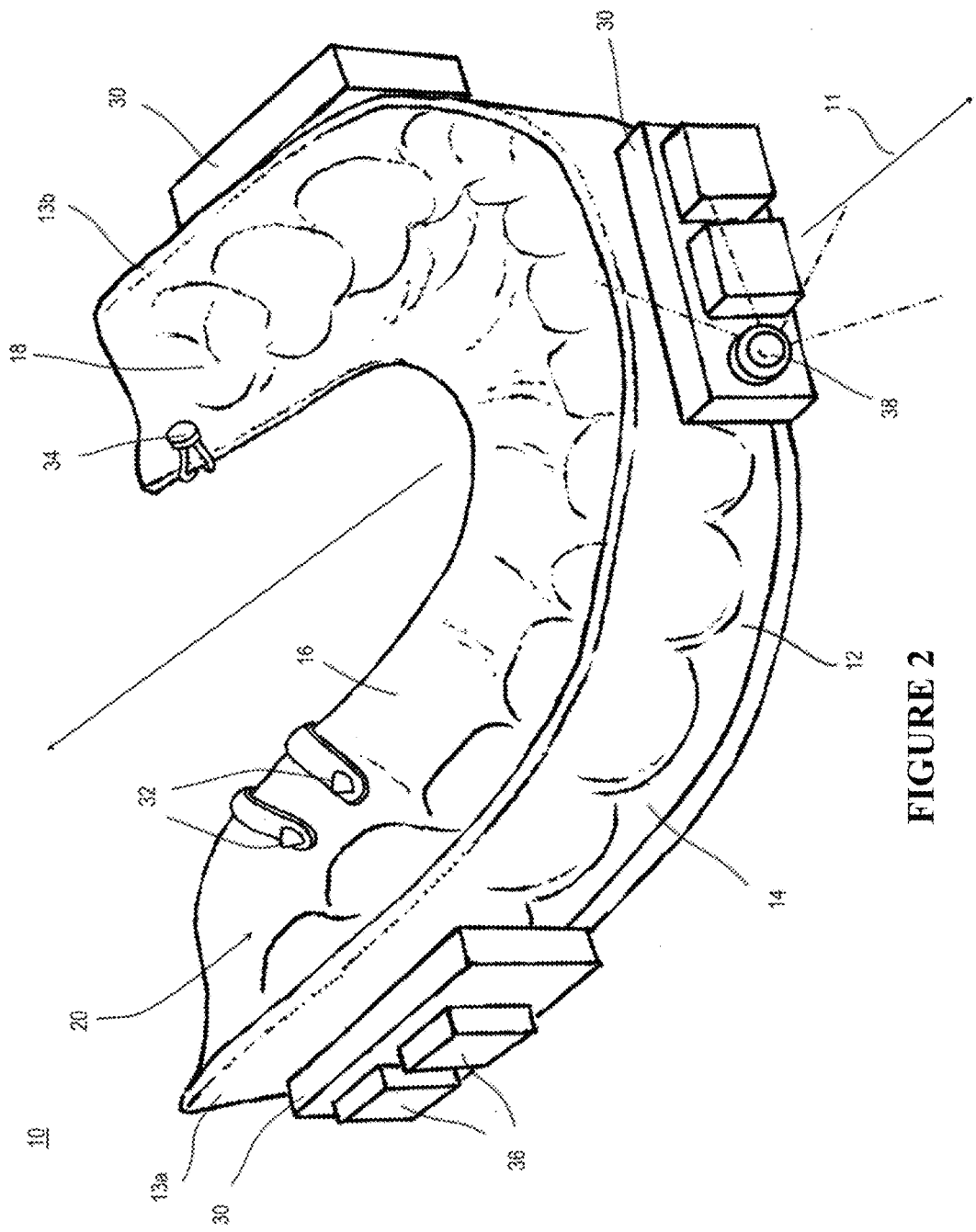
FIG. 2 is a perspective view of an exemplary mouth guard as disclosed herein.

In exemplary aspects, and with reference to FIGS. 1-2, a mouth guard 10 can be provided for engagement with the teeth of the subject. In these aspects, it is contemplated that the mouth guard 10 can comprise a U-shaped element 12 having an outer side wall 14, an inner side wall 16, and at least one biting surface 18. It is further contemplated that the outer side wall 14, the inner side wall 16, and the at least one biting surface 18 can cooperate to define at least one channel 20 configured to receive the upper teeth of the subject. In exemplary aspects, the channel 20 can be shaped to conform to the upper teeth of the subject. In these aspects, the channel 20 can be formed from a mold of the upper teeth of the subject. It is contemplated that a good fit between the mouth guard 10 and the upper teeth and gums can create a vacuum seal that prevents the mouth guard from being loose and rattling against the teeth during head impacts. In use, it is contemplated that the mouth guard 10 can be tightly fitted to the upper teeth and gums of the subject and be configured for loose engagement with the lower teeth of the subject.

In one aspect, and with reference to FIG. 2, the mouth guard 10 can comprise a plurality of measurement assemblies 30 operatively associated with the U-shaped element 12. In this aspect, it is contemplated that the plurality of measurement assemblies 30 can be spaced about the U-shaped element 12 at distinct locations as further disclosed herein. As further disclosed herein, it is contemplated that each measurement assembly 30 can comprise at least one of an electrode 32, a sensor 34 (e.g., a temperature sensor, a blood pressure sensor, and/or a heart rate sensor), and an accelerometer 36. Optionally, it is contemplated that at least one measurement assembly 30 of the plurality of measurement assemblies can comprise a light emitting diode (LED) 38 as further disclosed herein.

In an exemplary optional aspect, the plurality of measurement assemblies 30 can comprise a plurality of electrodes 32 operatively associated with the U-shaped element 12. In this aspect, it is contemplated that the plurality of electrodes 32 can be spaced from one another about the U-shaped element 12. It is further contemplated that each electrode 32 of the plurality of electrodes can be configured for contact with a portion of the mouth of the subject, including, for example and without limitation, the gums (interior and/or exterior gingiva), cheeks, lips, hard palate, soft palate (particularly, for example, portions of the soft palate proximate the palatine artery), and tongue of the subject. In exemplary aspects, and with reference to FIG. 2, it is contemplated that the plurality of electrodes 32 can be secured to the inner side wall of the U-shaped element 12 by a spring or other conventional coupling means such that pressure is maintained between the electrodes and the gums of the subject. Alternatively, in other exemplary aspects, it is contemplated that the plurality of electrodes 32 can be secured to the outer side wall 14 of the U-shaped element 12 using conventional coupling means.

In various aspects, the plurality of electrodes 32 can comprise at least three electrodes. In one exemplary aspect, the plurality of electrodes 32 of the mouth guard 10 can comprise three electrodes positioned at three distinct locations about the U-shaped element 12, as shown in FIGS. 1 and 2. In this aspect, it is contemplated that the plurality of electrodes 32 can be oriented within a substantially common plane. In exemplary aspects, the three distinct locations can correspond to first, second, and third locations spaced from one another about an arc defined by the U-shaped element 12. In these aspects, it is contemplated that the U-shaped element can define opposed first and second ends 13a, 13b. It is further contemplated that the U-shaped element 12 can be substantially symmetrical about a central axis 11. In exemplary aspects, it is contemplated that the first location can be proximate the first end 13a of the U-shaped element 12, the second location can be proximate the second end 13b of the U-shaped element, and the central axis 11 can intersect (and, optionally, substantially bisect) the third location. Thus, it is contemplated that the three distinct locations at which the plurality of electrodes 32 (and the plurality of measurement assemblies 30) are positioned can correspond to: (1) a position just outside the right molars of the subject; (2) a position just outside the left molars of the subject; and (3) a position just in front of the central incisors of the subject.

Optionally, in an additional aspect, the plurality of measurement assemblies 30 of the mouth guard 10 can comprise a plurality of temperature sensors. In this aspect, each temperature sensor of the plurality of temperature sensors can be configured to produce a temperature signal indicative of the temperature within the mouth of the subject.

Optionally, in another aspect, the plurality of measurement assemblies 30 of the mouth guard 10 can comprise a plurality of heart rate sensors. In this aspect, each heart rate sensor of the plurality of heart rate sensors can be configured to produce a heart rate signal indicative of the heart rate of the subject.

Optionally, in still another aspect, the plurality of measurement assemblies 30 of the mouth guard 10 can comprise a plurality of blood pressure sensors. In this aspect, each blood pressure sensor of the plurality of blood pressure sensors can be configured to produce a blood pressure signal indicative of the blood pressure of the subject.

Optionally, in a further aspect, it is contemplated that the plurality of measurement assemblies 30 of the mouth guard 10 can comprise a plurality of accelerometers 36. In this aspect, it is contemplated that each accelerometer 36 of the plurality of accelerometers can be configured to produce an output signal indicative of the acceleration (e.g., linear acceleration) of the accelerometer. Optionally, in some exemplary aspects, the plurality of accelerometers 36 can be configured to produce an output signal indicative of the linear and angular acceleration experienced by the mouth guard 10 and/or head of the subject. It is contemplated that the acceleration, the time rate of change of the acceleration, and other characteristics of the acceleration can be indicative of the severity of the head impact experienced by the subject. Optionally, each accelerometer 36 of the plurality of accelerometers can be configured to produce an output signal indicative of the impact force experienced by the accelerometer. In exemplary aspects, the plurality of accelerometers 36 of the mouth guard 10 can comprise microelectromechanical system (MEMS) accelerometers. It is further contemplated that the MEMS accelerometers can be provided on a chip.

In another aspect, the plurality of accelerometers 36 of the mouth guard 10 can optionally comprise nine single-axis accelerometers (capable of measuring linear acceleration in a single axis) positioned at the three distinct locations about the U-shaped element 12. In this aspect, three orthogonal single-axis accelerometers can be positioned in a cluster at each of the three distinct locations. Alternatively, the plurality of accelerometers 36 of the mouth guard 10 can comprise three three-axis accelerometers (capable of measuring linear acceleration in three axes), with one accelerometer positioned at each of the three distinct locations. In exemplary aspects, when the plurality of accelerometers 36 are positioned at three distinct locations and positioned and oriented within a common plane, it is contemplated that the plurality of accelerometers can comprise three two-axis accelerometers, with one two-axis accelerometer positioned at each of the three distinct locations. In further exemplary aspects, when the plurality of accelerometers 36 are positioned at three distinct locations and positioned and oriented within a common plane, it is contemplated that the plurality of accelerometers can comprise six single-axis accelerometers, with a cluster of two single-axis accelerometers being positioned at each of the three distinct locations.

Although described herein as being positioned at three distinct locations within the mouth of the subject, it is contemplated that other positions and orientations of the plurality of measurement assemblies 30 (comprising electrodes 32, sensors 34, and/or accelerometers 36) can be employed to determine the at least one physiological condition of the subject. It is further contemplated that the plurality of measurement assemblies 30 can comprise any number of measurement assemblies (and thus, any number of electrodes 32, sensors 34, and/or accelerometers 36) that provide sufficient data to determine the at least one physiological condition of the subject. For example, it is contemplated that the plurality of measurement assemblies 30 can comprise more than three measurement assemblies.

In other exemplary aspects, the disclosed mouth guard 10 can comprise one or more hard acrylic materials formed over a cast made from impressions of the subject's teeth and gums and hard and soft palate according to conventional methods. In still other exemplary aspects, it is contemplated that the mouth guard 10 can comprise one or more thermoplastic materials heated by an infrared (IR) heating lamp and be vacuum formed over a cast made from impressions of the subject's teeth and gums and hard and soft palate according to conventional methods. In still other exemplary aspects, it is contemplated that the mouth guard 10 can comprise one or more thermoplastic materials that can be softened in hot water and then placed in the mouth of the subject and fit to the upper teeth of the subject, as is conventionally known in the art. In these aspects, it is contemplated that the number of dental clinic visits and the amount of laboratory costs can be significantly reduced. It is further contemplated that the electrodes 32, sensors 34, accelerometers 36, and processing circuitry 60 described herein can be configured to withstand temperatures far above the boiling point of water and can easily survive such a fitting.

Optionally, in one aspect, the plurality of electrodes 32 (and, optionally, the plurality of sensors 34 and/or accelerometers 36) can be electrically coupled to a plurality of printed circuit board (PCB) assemblies. For example, in one exemplary aspect, the plurality of PCB assemblies can comprise three PCB assemblies spaced about the mouth guard. In this aspect, it is contemplated that when the plurality of measurement assemblies 30 comprises three measurement assemblies, each PCB assembly can be configured for electrical coupling to the electrodes 32, sensors 34, and/or accelerometers 36 of a respective measurement assembly.

Alternatively, in other exemplary aspects, it is contemplated that the plurality of electrodes 32 (and, optionally, the plurality of sensors 34 and/or accelerometers 36) can be directly electrically coupled to the processing circuitry 60.

Formation of the Mouth Guard

Figure 4:
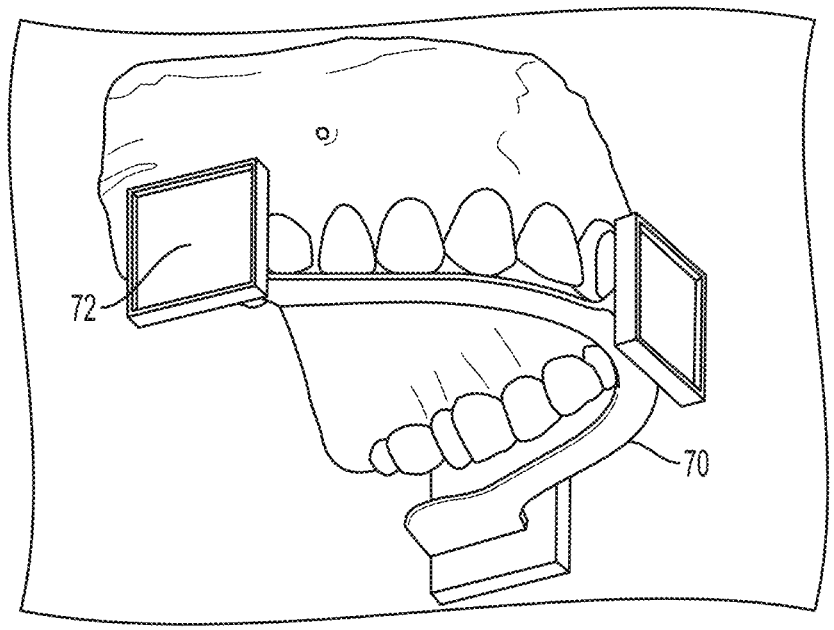
FIG. 4 shows the fitting of a bridge element to three-dimensional scans of the upper jaw of a subject as disclosed herein FIG. 5 displays an image of a bridge element printed using a three-dimensional printer.

In exemplary aspects, the mouth guard 10 can be formed from impressions of the teeth and gums and hard and soft palate of the upper and lower jaws of the subject. In these aspects, the impressions can be used to form a cast of the subject's teeth and gums using conventional methods. The casts of the teeth and gums of the subject can then be scanned using a three-dimensional (3-D) scanner. Alternatively, in other exemplary aspects, an intraoral 3-D dental scan of at least the teeth, gums, and soft and hard palate of the upper and lower jaws of the subject can be performed. It is further contemplated that the 3-D scans of the casts can then be uploaded to a 3-D solid modeling software package. As shown in FIG. 4, a bridge element 70 can be fitted to the scans. It is contemplated that the bridge element 70 can be configured to fit to the upper jaw such that there is about 2 mm of clearance between the bridge element and the teeth and gums of the subject. It is further contemplated that a 2 mm thick thermoplastic sheet can be vacuum-formed to the cast of the teeth and gums of the upper jaw of the subject and trimmed to form the mouth guard. Clearance can be confirmed between the bridge and the lower jaw, and the bridge can be adjusted as necessary.

Figure 5:
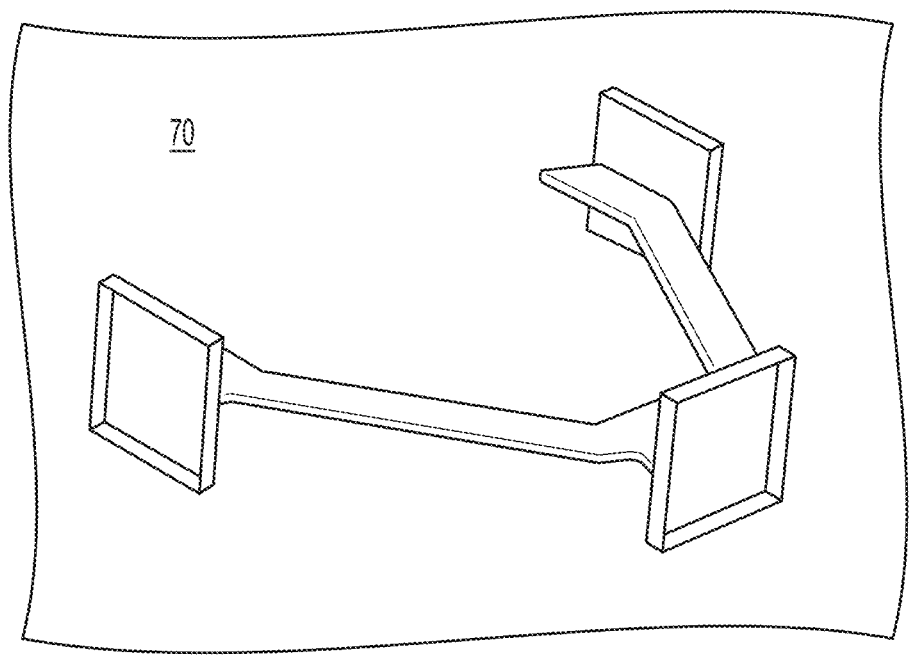

Optionally, in some exemplary aspects, it is contemplated that at least a portion of the mouth guard 10 can be printed with a 3-D printer as is known in the art. As depicted in FIG. 5, it is contemplated that the bridge can be constructed of Acrylonitrile Butadiene Styrene (ABS) or other plastic material using a 3-D printer as is known in the art. It is further contemplated that the bridge 70 can be affixed to the mouth guard using medical-grade adhesive. Alternatively, in other exemplary aspects, it is contemplated that substantially the entire mouth guard, either as one piece or in multiple pieces to be assembled, comprising either a single material or a plurality of materials, can be printed with a 3-D printer. In exemplary aspects, it is contemplated that a second soft layer of thermoplastic material can be heated and vacuum-formed over and bonded to the mouth guard 10, the bridge element 70, and at least a portion of the processing circuitry 60. In these aspects, it is contemplated that the second layer of thermoplastic material can substantially encapsulate and seal the processing circuitry and thereby protect the processing circuitry. It is further contemplated that the second layer of thermoplastic material can be shaped to make the mouth guard more ergonomic. In other exemplary aspects, it is contemplated that a combination of the steps of the manufacturing processes disclosed above can be used to form the mouth guard.

In another exemplary aspect, the bridge element 70 can be coupled to three receptacles 72 configured to operatively receive one or more of an electrode 32, accelerometer 36, and sensor 34 as disclosed herein. Optionally, it is contemplated that each receptacle 72 can be configured to receive a printed circuit board (PCB) assembly as described herein. In this aspect, the three receptacles 72 can be spaced about the mouth guard and positioned at respective positions. For example, a first receptacle can be positioned just outside the right molars of the subject, a second receptacle can be positioned just outside the left molars of the subject, and the third receptacle can be positioned just in front of the central incisors of the subject. In exemplary aspects, each receptacle can be configured to receive a respective PCB assembly. In these aspects, each PCB assembly can be affixed to the receptacles by medical-grade adhesive or another conventional adhesive, provided the adhesive is safe for usage within the mouth of a subject. It is further contemplated that the PCB assemblies, after being positioned within a respective receptacle, can be wired and sealed. Optionally, it is contemplated that each electrode 32 of the plurality of electrodes can be associated with a respective PCB assembly of the plurality of PCB assemblies. Similarly, it is contemplated that each sensor 34 and accelerometer 36 of the mouth guard 10 can be associated with a respective PCB assembly of the plurality of PCB assemblies. However, in some aspects, as further described herein, rather than being coupled to PCB assemblies, it is contemplated that each electrode 32, sensor 34, and/or accelerometer 36 of the mouth guard 10 can be directly electrically connected to the processing circuitry 60. In exemplary aspects, it is contemplated that the bridge element 70 can define the three receptacles 72. In these aspects, it is contemplated that the three receptacles 72 can be integrally formed with the bridge element 70. Thus, it is contemplated that the receptacles 72 can optionally be integrally formed with the bridge element 70.

In operation, it is contemplated that the bridge element 70 can ensure that the electrodes 32, accelerometers 36, and/or sensors 34 disclosed herein are properly positioned. For example, it is contemplated that the bridge element 70 can be configured to ensure that the bottom edges of each receptacle 72 are positioned substantially within a common plane. It is further contemplated that the receptacles of the bridge element can be spaced such that the left and right receptacles are substantially symmetrically positioned relative to the sagittal plane of the subject. It is still further contemplated that the center receptacle can be positioned such that it is substantially bisected by the sagittal plane of the subject.

Figure 15:
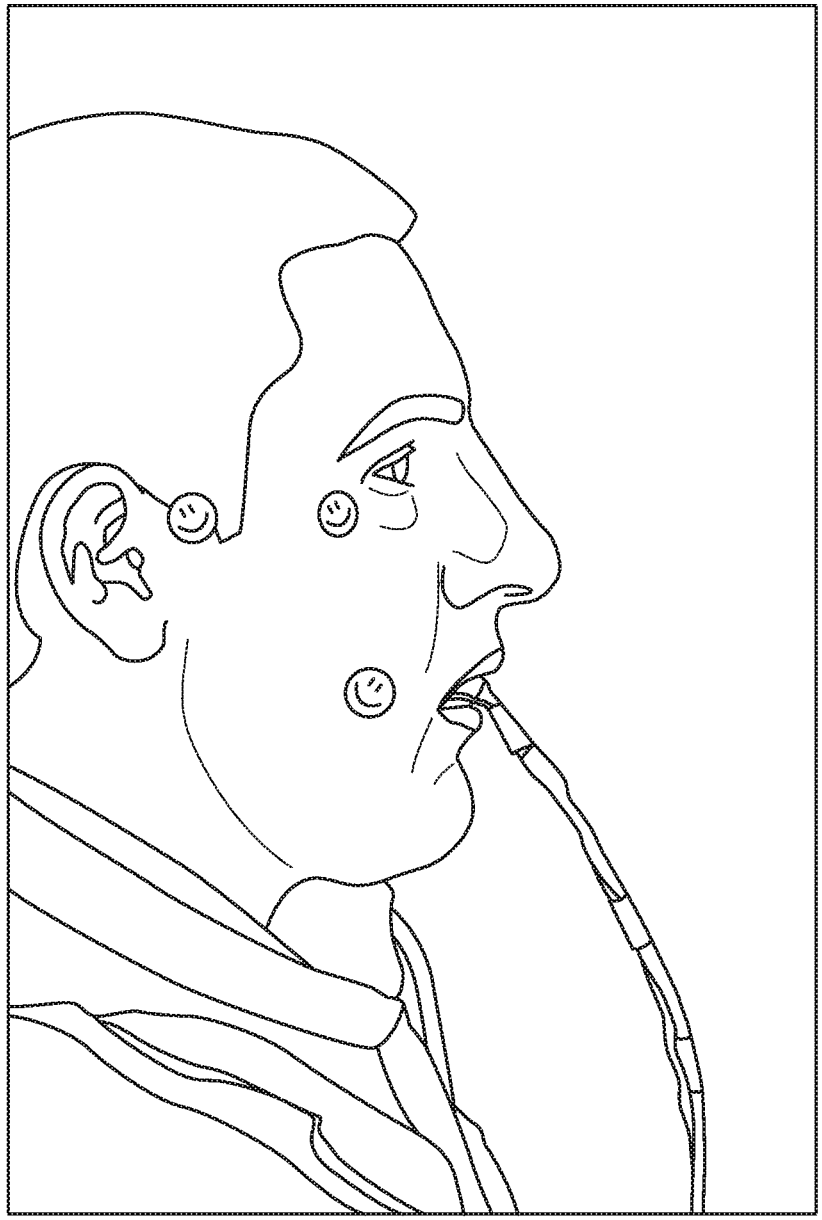
FIG. 15 depicts the use of biometric markers to determine the linear and angular positioning of a mouth guard relative to the head of a subject as disclosed herein.

It is contemplated that the linear and angular positions of the mouth guard 10 relative to the head of the subject can be identified using biometric markers, such as those shown in FIG. 15. The center of mass of the head of the subject is positioned just beneath the zygomatic arch, just in front of the ear. The center of mass of the head of the subject can generally be found by running one's fingers along the crest of the cheekbone ridge that runs roughly from the eye socket (corresponding to the smiley face marker closest to the eye) back to the ear (corresponding to the smiley face marker closest to the ear). The left and right crest of the cheekbone ridge generally corresponds to the transverse plane of the head. The transverse plane intersects the sagittal plane, and a third plane, the coronal plane of the head, is orthogonal to those two planes. All three planes intersect at the center of mass of the head. The intersections of the planes form the fore-aft, left-right, and up-down directions of the head. The right PCB of the mouth guard can be positioned just inside the cheek and is found by palpating the cheek (corresponding to the lowest smiley face marker). It is contemplated that the front PCB can be visible if the subject's lips are parted. It is contemplated that other biometric markers may be identified as important for determining the severity of head impact.

Similar positional information for the head of the subject can be determined for the opposite (left) side of the head of the subject, and the positional values are then averaged to give the final positional information for the head of the subject. Using these average values, the linear and angular positions of the mouth guard relative to the head of the subject can be determined.

Figure 6:
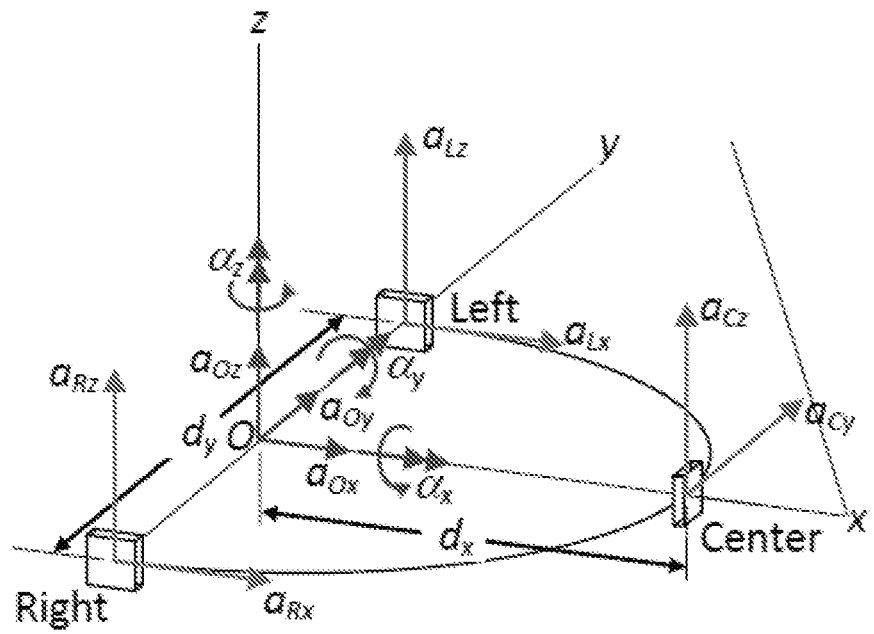
FIG. 6 depicts an exemplary local mouth guard coordinate system having axes x, y, and z and origin O. In the exemplary mouth guard system shown in FIG. 6, three 2-axis accelerometers (a total of six accelerometers to measure linear acceleration in the directions shown by the arrows originating from the respective accelerometers) are positioned and oriented in the mouth guard for accurate and precise determination of the angular and linear accelerations of the mouth guard origin O, marked by the arrows originating from point O.
Figure 7:
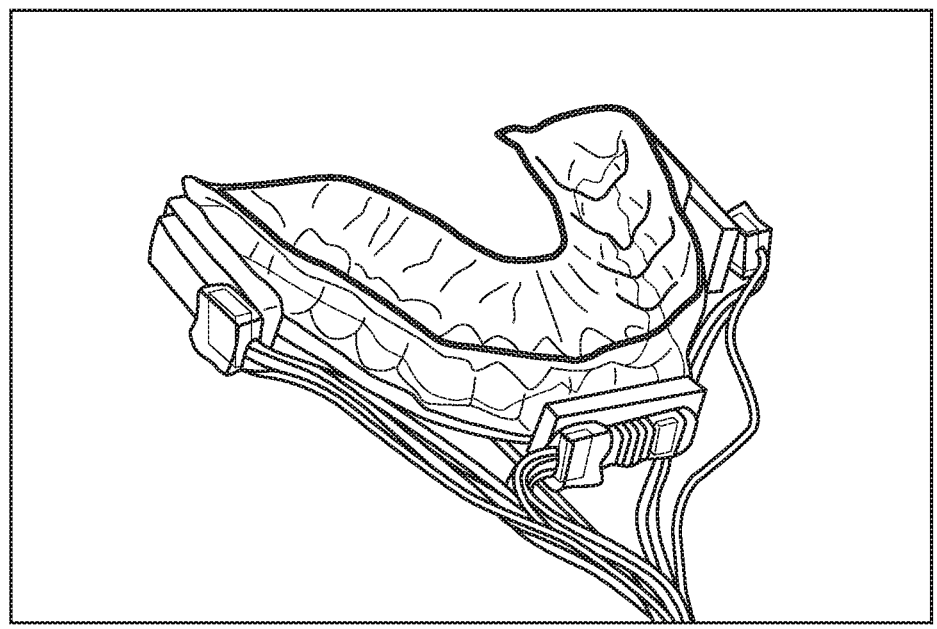
FIG. 7 displays an exemplary thermoplastic mouth guard with a bridge element, two PCB assemblies (each having two accelerometers), wiring, and sealant. A third PCB (having two accelerometers) is hidden from view on the left side of the mouth guard bridge element.

In use, and with reference to FIGS. 1, 6, and 7, it is contemplated that the left PCB assembly (and associated accelerometers) can be configured to measure acceleration in the up-down and fore-aft directions, the right PCB assembly (and associated accelerometers) can be configured to measure acceleration in the up-down and fore-aft directions, and the central PCB assembly (and associated accelerometers) can be configured to measure acceleration in the left-right and up-down directions. The forward direction corresponds with the x direction, the leftward direction corresponds with the y-direction, and the upward direction corresponds with the z direction.

In exemplary aspects, it is contemplated that the outputs of the accelerometers of the disclosed mouth guard can be analyzed with respect to a 3-axis coordinate system using the helmet and/or the transformation algorithms disclosed in U.S. Nonprovisional patent application Ser. No. 14/144,791, filed Dec. 31, 2013, which is incorporated herein by reference in its entirety.

In further exemplary aspects, it is contemplated that a mouth guard as disclosed herein can be provided in conjunction with a conventional helmet 40, such as, for example and without limitation, a sports helmet (e.g., a football helmet, a hockey mask, a baseball helmet, and the like), a military helmet, or an industrial helmet. In these aspects, it is contemplated that the mouth guard can be operatively coupled to a tether, such as a strap 50, which in turn is operatively coupled to a face mask or other selected portion of the helmet. It is further contemplated that the mouth guard can be coupled to the helmet such that the mouth guard is positioned proximate the mouth of a subject when the subject wears the helmet. An exemplary configuration of a mouth guard tethered to a sports helmet is depicted in FIG.

14. In exemplary aspects, it is contemplated that the strap 50 can comprise at least one wire 52 for establishing electrical communication between the mouth guard 10 and processing circuitry 60 positioned within the helmet 40, as further disclosed herein.

The Processing Circuitry

Figure 3:
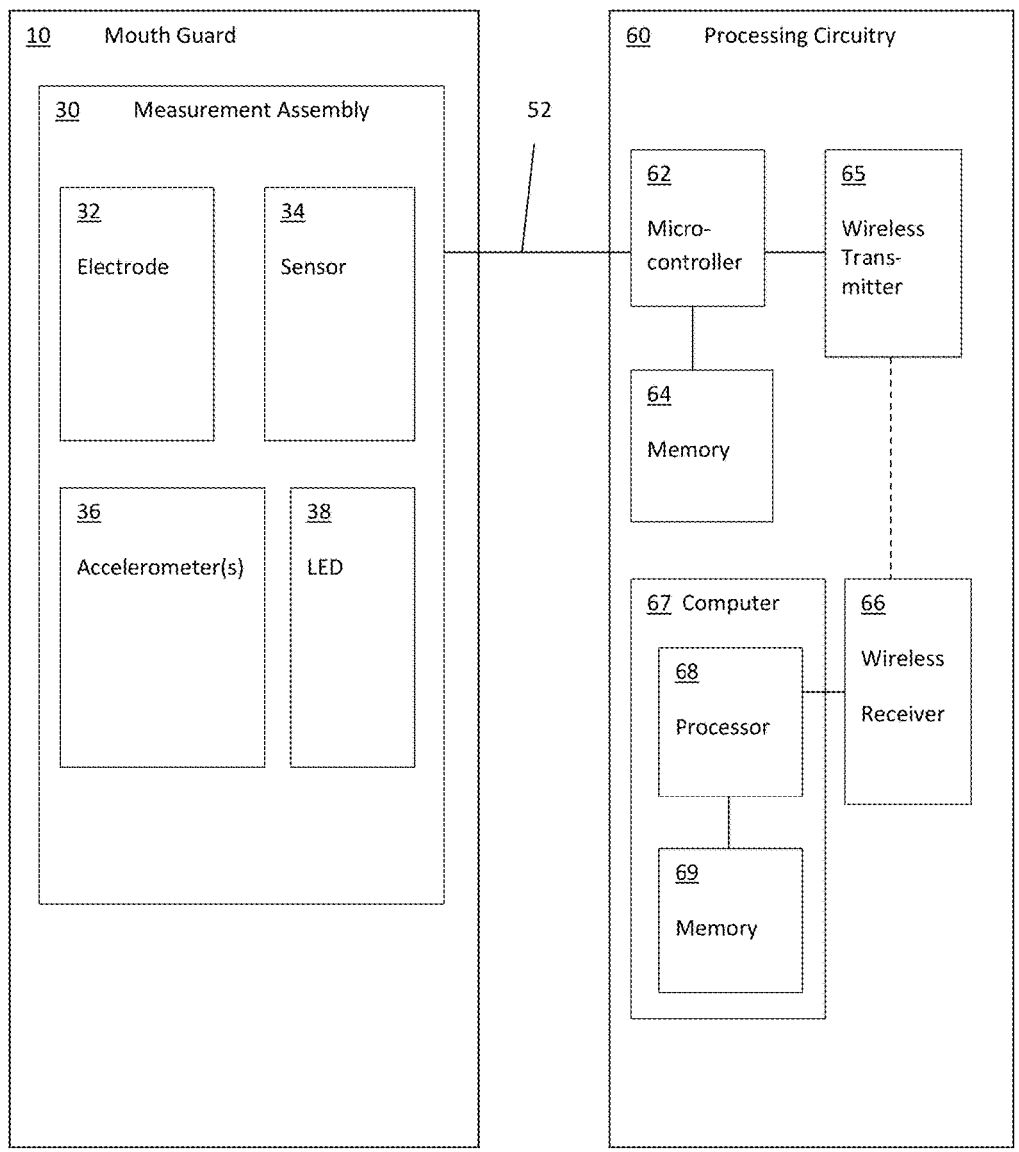
FIG. 3 is a schematic diagram depicting a measurement system comprising a mouth guard and processing circuitry as disclosed herein.

In a further aspect, and with reference to FIG. 3, the electrodes 32, accelerometers 36, and/or sensors 34 of the mouth guard 10 can be configured for operative communication with processing circuitry 60. In this aspect, the processing circuitry 60 can optionally be configured to measure the impedance between respective electrodes of the plurality of electrodes 32. It is contemplated that the measured impedance between respective electrodes of the plurality of electrodes can be indicative of the at least one physiological condition of the subject. In exemplary aspects, the processing circuitry 60 can function as an integrated circuit. In other exemplary aspects, the plurality of electrodes 32 can be embedded in the mouth guard 10. Optionally, it is contemplated that at least portions of the processing circuitry 60 can be embedded in the mouth guard 10.

In other exemplary aspects, it is contemplated that the plurality of temperature sensors can be configured for operative communication with the processing circuitry. In these aspects, it is contemplated that each temperature sensor of the plurality of temperature sensors can be configured to transmit its temperature signal to the processing circuitry.

In further exemplary aspects, it is contemplated that the plurality of heart rate sensors can be configured for operative communication with the processing circuitry. In these aspects, it is contemplated that each heart rate signal of the plurality of heart rate sensors can be configured to transmit its heart rate signal to the processing circuitry.

In other exemplary aspects, it is contemplated that the plurality of blood pressure sensors can be configured for operative communication with the processing circuitry. In these aspects, it is contemplated that each blood pressure sensor of the plurality of blood pressure sensors can be configured to transmit its blood pressure signal to the processing circuitry.

In additional exemplary aspects, it is contemplated that the plurality of accelerometers 36 can be configured for operative communication with the processing circuitry 60. In these aspects, it is contemplated that each accelerometer of the plurality of accelerometers can be configured to transmit its output signal to the processing circuitry.

In still a further aspect, the electrodes 32, sensors 34, and/or accelerometers 36 of the mouth guard 10 can be in operative communication with at least one power source. In this aspect, the at least one power source can be in operative communication with the processing circuitry such that the at least one power source is configured to power the electrodes, sensors, and/or accelerometers of the mouth guard and the processing circuitry. It is contemplated that the at least one power source can be a conventional battery, capacitor, or electromagnetic power source. Optionally, it is further contemplated that the at least one power source can be rechargeable through a first port defined in the mouth guard. It is still further contemplated that the at least one power source can be removable and replaceable. In an exemplary aspect, it is contemplated that the at least one power source can be an electric generator that is powered by mechanical energy received from the subject. In this aspect, it is contemplated that the electric generator can be configured to convert mechanical energy applied to the mouth guard by the subject (through, for example, biting down) into electrical energy. It is contemplated that the electric generator can optionally be a piezoelectric generator comprising one or more materials that exhibit the piezoelectric effect, such as, for example and without limitation, quartz. When coupled with appropriate circuitry, it is contemplated that such piezoelectric generators can be configured to generate electrical energy from cyclic mechanical strain.

In one aspect, the processing circuitry 60 can comprise at least one memory 64 in operative communication with the plurality of electrodes 32 (and, optionally, the plurality of sensors 34 and/or the plurality of accelerometers 36) of the mouth guard 10. In this aspect, it is contemplated that the at least one memory 64 can be configured to receive and store the measured impedances between respective electrodes of the mouth guard. Optionally, the at least one memory can be configured to receive and store the signals and/or outputs of the sensors and/or accelerometers of the mouth guard. In some aspects, the at least one memory can be coupled to the mouth guard. However, in other alternative aspects, it is contemplated that the at least one memory can be positioned at a remote location from the subject, such as, for example and without limitation, within a remote computer.

In another aspect, the processing circuitry can comprise at least one wireless transmitter 65 in operative communication with at least one of the at least one memory 64, the plurality of electrodes 32 of the mouth guard, the plurality of sensors 34 of the mouth guard, and the plurality of accelerometers 36 of the mouth guard. In this aspect, it is contemplated that the at least one wireless transmitter 65 can be configured to wirelessly transmit one or more outputs stored on the at least one memory 64. Although a wireless transmitter is preferred, it is contemplated that the at least one memory and the plurality of electrodes (and, optionally, the plurality of sensors and/or the plurality of accelerometers) can be connected to one another by a conventional hard-wired connection.

In an additional aspect, it is contemplated that the processing circuitry can comprise an analog-to-digital converter as is conventionally known in the art. In this aspect, it is contemplated that the analog-to-digital converter can be operatively coupled to and positioned between the electrodes and the at least one memory. Similarly, it is contemplated that the analog-to-digital converter can be operatively coupled to and positioned between the sensors and the at least one memory and/or the accelerometers and the at least one memory. It is further contemplated that the analog-to-digital converter can be configured to receive the measured impedances, the signals of the sensors, and/or the outputs of the plurality of accelerometers and convert the various signals and outputs into corresponding digital signals configured for further processing by the processing circuitry.

In some optional aspects, the processing circuitry 60 can comprise a microcontroller 62 in operative communication with one or more components of the processing circuitry. In these aspects, it is contemplated that the microcontroller 62 can comprise hardware and software that are configured to control the operation of the components of the processing circuitry 60 in operative communication with the microcontroller. For example, it is contemplated that the microcontroller can be configured to initiate transmission of outputs stored on the at least one memory.

In exemplary aspects, the microcontroller 62 can be positioned in operative communication with the at least one wireless transmitter 65. In these aspects, it is contemplated that the microcontroller 62 can optionally be configured to selectively transmit the stored outputs (following analog-to-digital conversion, as appropriate) of the electrodes 32, sensors 34, and/or accelerometers 36 to a server, which, in some aspects, can be in communication with a wireless receiver 66. It is further contemplated that the server can be positioned remotely from the subject. In exemplary aspects, the server can be provided as part of a computer 67 having a processor 68 and a memory 69 in operative communication with the processor. It is further contemplated that the wireless transmitter 65 can optionally be a wireless transmitter-receiver that also functions as a wireless receiver (in addition to a wireless transmitter). It is still further contemplated that the wireless receiver 66 can optionally be a wireless transmitter-receiver that also functions as a wireless transmitter (in addition to a wireless receiver). Optionally, it is contemplated that the processor 68 of the computer can initiate transmission of the stored outputs of the electrodes 32, sensors 34, and/or accelerometers 36 to the server (computer 67).

In further exemplary aspects, it is contemplated that the processing circuitry can comprise means for generating an alarm in response to one or more of the impedance measurements, signals of the sensors, and/or output signals of the plurality of accelerometers. In these aspects, it is contemplated that the means for generating an alarm can comprise a conventional device for selectively generating optical, thermal, vibrational, and/or audible alarm signals. In additional exemplary aspects, it is contemplated that the processing circuitry can be configured to identify an alarm condition corresponding to a threshold value of one or more of the impedance measurements, signals of the sensors, and/or accelerometer output signals. In these aspects, it is contemplated that the processing circuitry can be configured to generate an alarm in response to the alarm condition. Optionally, in additional aspects, it is contemplated that the plurality of electrodes can be configured to apply an electrical pulse to surrounding tissue in response to the alarm condition. In these aspects, it is contemplated that pulses applied to the tongue of the subject in this manner can be identified according to region of the tongue and/or the associated taste response of the subject.

Optionally, in one exemplary aspect, the alarm condition can be triggered when a threshold body temperature (measured from the mouth and reflected in the temperature output signals) is reached. In another optional exemplary aspect, it is contemplated that the alarm condition can be triggered when a threshold head acceleration (measured from the mouth and reflected in the accelerometer output signals) is reached. In another optional exemplary aspect, it is contemplated that the alarm condition can be triggered when a threshold blood pressure (measured from the mouth and reflected in the signals produced by the blood pressure sensors) is reached. In still another optional exemplary aspect, it is contemplated that the alarm condition can be triggered when a threshold heart rate (measured from the mouth and reflected in the signals produced by the heart rate sensors) is reached. It is contemplated that the various alarm conditions can be identified with a conventional greater-than-less-than trigger with a requirement that a predetermined threshold value be surpassed for a selected period of time before the actual trigger is activated, thereby avoiding spurious triggers.

In another exemplary aspect, and with reference to FIGS. 1-2, the means for generating an alarm can comprise at least one visual indicator, such as, for example and without limitation, a light emitting diode (LED) 38 or other selectively illuminated indicator. In this aspect, it is contemplated that the at least one visual indicator can be activated (illuminated) in response to an alarm condition as described herein.

Figure 14:
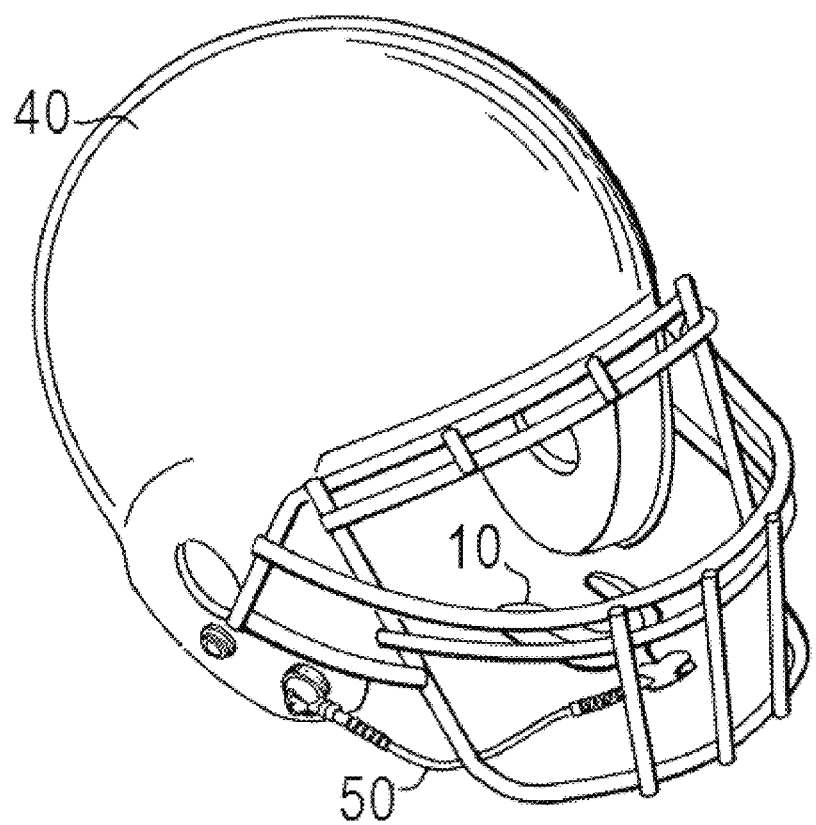
FIG. 14 is an image of an exemplary helmet and a tethered mouth guard as disclosed herein.

In exemplary aspects, as depicted in FIG. 14, it is contemplated that the mouth guard 10 can be provided in association with a helmet 40 as further disclosed herein. In these aspects, it is contemplated that at least one component of the processing circuitry 60 can be embedded within or otherwise operatively attached to the helmet 40. For example, in one optional aspect, it is contemplated that the mouth guard 10 can be operatively associated with the electrodes 32, sensors 34, and/or accelerometers 36, while remaining components of the processing circuitry 60, such as, for example and without limitation, the microcontroller 62, the memory 64, the wireless transmitter 65, the charging circuit, and the battery, can be embedded within or otherwise operatively attached to the helmet 40. In this aspect, and as further described herein, it is contemplated that the processing circuitry can comprise at least one wire 52 operatively coupled to and extending between the electrodes 32, sensors 34, and/or accelerometers 36 of the mouth guard 10 and the microcontroller 62 within the helmet 40. It is further contemplated that the at least one wire 52 can be positioned within the strap 50 that secures the mouth guard 10 to the helmet 40.

It is contemplated that the way in which the measurement data is stored and recovered can significantly impact the complexity, size and power requirements of the device. For example, it is contemplated that storing the data for downloading using a hardwire connection at a later time can significantly reduce the complexity, size and power requirements of the mouth guard electronics.

Exemplary Methods

In use, the mouth guard, in conjunction with the processing circuitry, can be used in a method for determining one or more physiological conditions of the subject. In one aspect, the mouth guard can be positioned in engagement with at least one of the upper teeth and the lower teeth of the subject. In an additional aspect, the method can comprise measuring the impedance between respective electrodes of the plurality of electrodes. Optionally, the method can further comprise measuring the blood pressure of the subject. Optionally, the method can further comprise measuring the heart rate of the subject. Optionally, the method can further comprise measuring the temperature within the mouth of the subject. It is further contemplated that the method can further comprise measuring the acceleration (linear and/or angular) of the mouth guard. Optionally, it is still further contemplated that the method can comprise measuring the impact forces experienced by the mouth guard. It is contemplated that the accelerations measured by the accelerometers of the mouth guard can substantially correspond to the acceleration actually experienced by the head of the subject. In exemplary aspects, the method can comprise simultaneously measuring the impedance between respective electrodes, the temperature within the mouth of the subject, the blood pressure of the subject, the heart rate of the subject, the acceleration of the mouth guard, and/or the impact forces experienced by the mouth guard and/or the subject.

In a further aspect, the method can comprise transmitting the impedance measurements and/or the outputs of the temperature sensors and/or accelerometers of the mouth guard to the processing circuitry. In still a further aspect, the method can comprise, through the processing circuitry, determining the one or more physiological conditions of the subject. In this aspect, it is contemplated that the processing circuitry can be configured to identify one or more alarm conditions based upon the recorded impedance measurements, temperature signals, and/or accelerometer outputs. It is contemplated that, during a potentially concussive impact to the head, linear and angular accelerations of the head can be determined from the mouth guard accelerometer measurements. Immediately following a concussive impact to the head, it is contemplated that changes in biometrics, such as heart rate, breathing rate, blood pressure, and temperature, can occur. Thus, it is contemplated that the acceleration and biometric data together can provide a robust indicator of concussion.

In another exemplary method, it is contemplated that a database of impedance measurements can be developed into a tool for providing information to a subject or healthcare provider regarding historical physiological characteristics of the subject, thereby providing a means for determining unusual behaviors or conditions. In this aspect, the method can further comprise, through a processor in communication with the database, determining unusual behaviors and/or conditions. It is contemplated that the processor can be configured to identify alarm conditions as further disclosed herein.

In further exemplary aspects, it is contemplated that the disclosed mouth guard can be worn by athletes, soldiers, and/or industrial workers. For example, it is contemplated that the impedance measurements can be used to determine the respiration rate and/or respiration volume of the subject. It is further contemplated that the impedance measurements can be used to determine the moisture content within the mouth of the subject. It is still further contemplated that the impedance measurements can be used to determine the blood pressure of the subject. When multi-point impedance measurements are recorded using three or more electrodes, it is contemplated that variations between the impedance of surface and bulk tissue in the mouth of the subject can be identified. These variations can be used to determine hyperthermia and/or dehydration conditions when the subject is involved in activities during which the mouth of the subject is regularly filled with liquids (either for consumption or rinsing), such as, for example and without limitation, endurance swimming, water polo, and other water-related sports and occupations. In other exemplary aspects, it is contemplated that the impedance measurements can be used to determine whether the subject is breathing through his or her mouth or nasal cavity. In still further aspects, it is contemplated that the impedance measurements can be used to determine the frequency and/or duration of mouth closure and/or contact of the tongue to the roof of the mouth of the subject.

In operation, when non-periodic measurements (such as temperature) are used, it is contemplated that data points can be collected and then processed according to a predetermined calibration algorithm, such as a series of equations and/or a lookup table (including known physiological characteristics). When periodic measurements (where temporal characteristics are important) such as respiration and/or heart rate are used, a series of time-separated measurements can be collected. These data points can then be calibrated and transformed by a Fourier Transformation (or other conventional transformation). Following transformation, the peak(s) in a reasonable frequency range can be identified (such as, for example and without limitation, 0.1-1 Hz for respiration). The frequency and intensity of the largest peak(s) can then be identified to determine the rate and intensity of the periodic event. For example, if the primary peak in a respiratory measurement was centered at 0.3 Hz, then the measurement would be indicative of a respiratory rate of 18 breaths per minute.

In exemplary aspects, when the mouth guard comprises temperature sensors, it is contemplated that the temperature signals produced by the temperature sensors can be indicative of the temperature of surrounding tissue within the mouth of the subject and/or the temperature of inhaled and exhaled air. In these aspects, it is further contemplated that the temperature signals can be used in combination with the impedance measurements to more accurately identify hyperthermia and/or dehydration conditions. For example, because severe dehydration is often accompanied by fever and elevated respiratory rate (tachypnea) and hyperthermia is often accompanied by elevated respiratory rate, it is contemplated that the availability of information regarding the body temperature and respiratory rate and/or hydration of the soft palate can provide a more accurate prediction of hyperthermia and dehydration conditions. In additional exemplary aspects, it is contemplated that the mouth guard can be used to perform impedimetric heart rate monitoring. For example, because the mouth contains palatine arteries which undergo pronounced pressure and volumetric changes during a heart cycle, it is contemplated such changes can be measured via impedance by the mouth guard and/or via a pressure transducer.

The following examples are offered by way of illustration and not by way of limitation.

Experimental Example One

Figure 8:
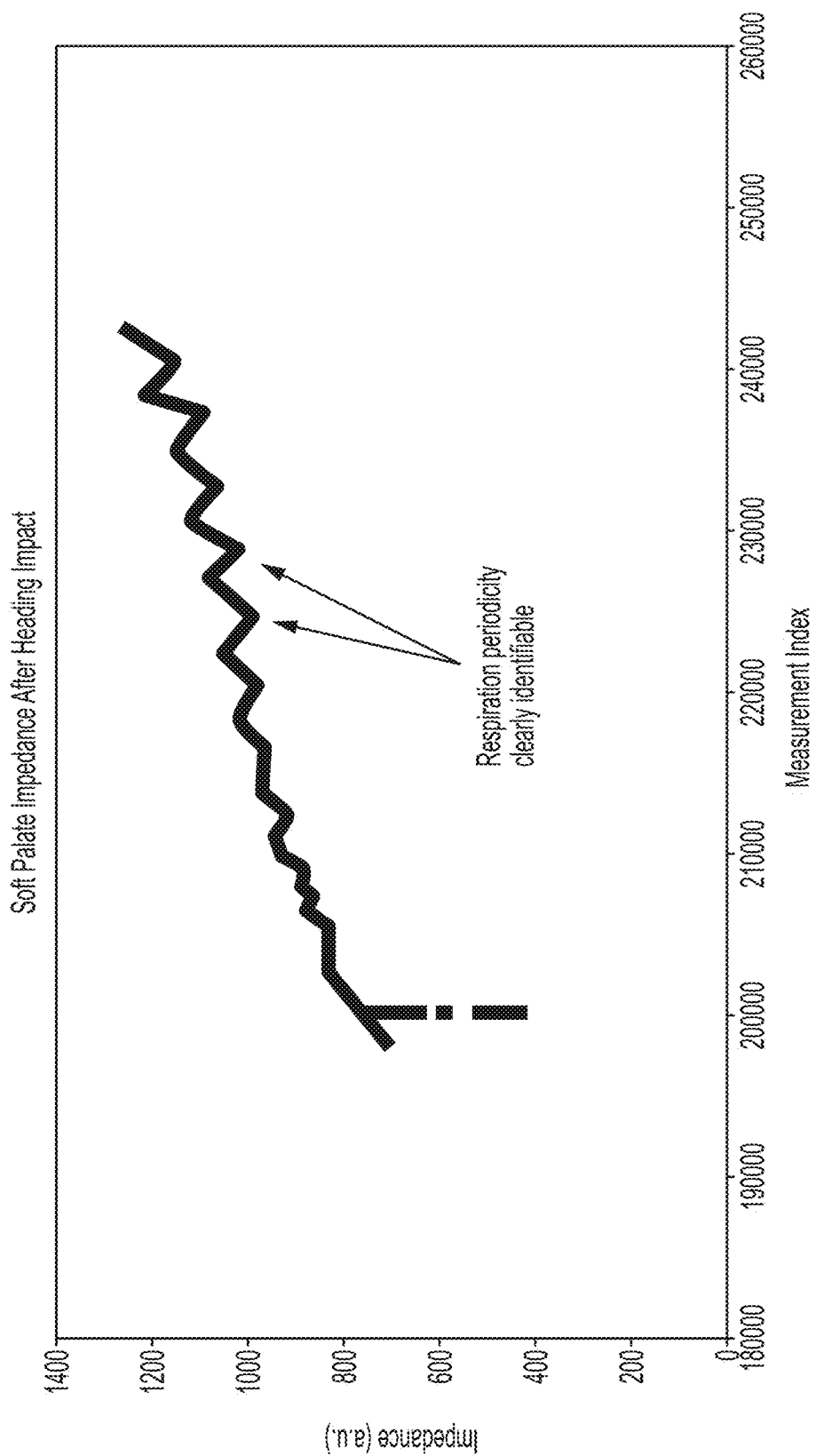
FIG. 8 is a graph depicting the changes in impedance within the mouth of a subject during soccer ball heading, as measured by a mouth guard as disclosed herein.

FIG. 8 shows data collected by an exemplary mouth guard during measurement of the impedance of the soft palate of a subject after the subject experienced a blow to the head. Electrodes on the mouth guard contacted the sides of the soft palate near the $2^{nd}$ molars of the subject. The instrumented mouth guard measured the impedance between the two electrodes through the soft palate tissue. As shown in FIG. 8, the impedance of the soft palate tissue increased and decreased with respiratory events. Therefore, these measurements were useful for determining respiratory function parameters, including respiratory rate.

Figure 9:
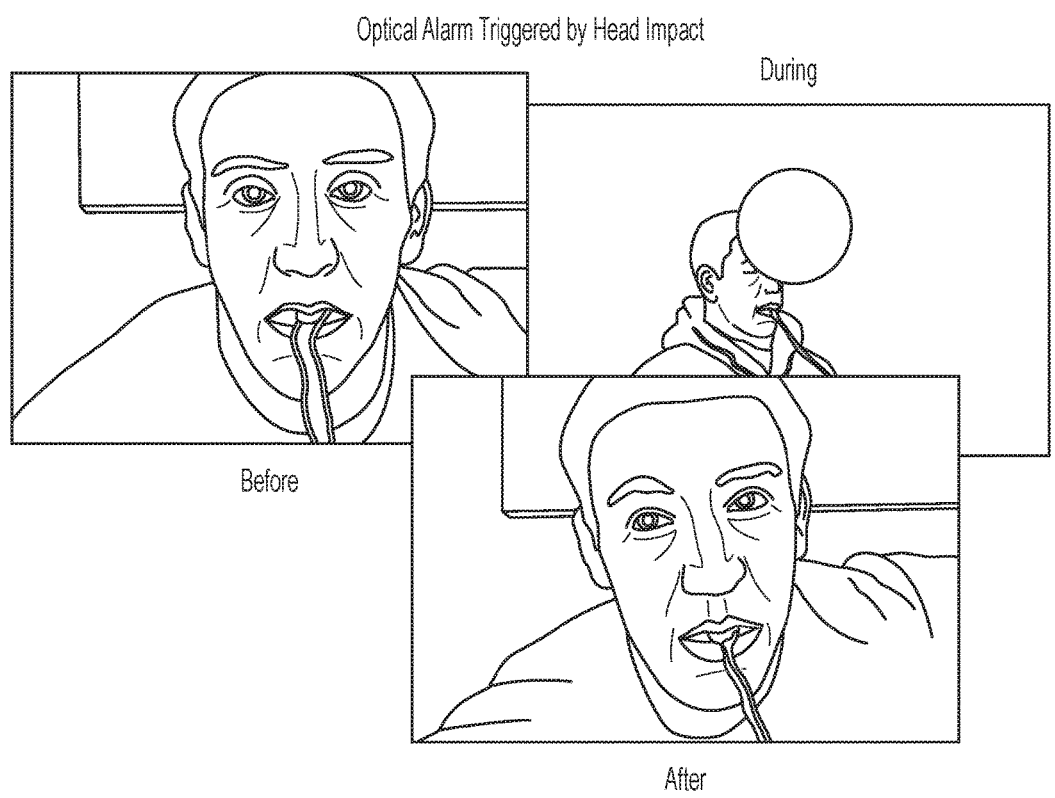
FIG. 9 depicts the experimental setup and procedure that were used to gather the data displayed in FIG. 8.

FIG. 9 shows the functionality of an exemplary visual impact indicator of a mouth guard as disclosed herein. A high-intensity light-emitting diode (LED) was installed with the mouth guard so that the subject's mouth would be illuminated by the LED. The LED was configured to emit light of a selected color indicating a predetermined condition, such as whether an acceleration threshold was reached or whether a signal was received by a wirelessly connected server to change the light color). Optionally, the predetermined condition can correspond to an alarm condition as disclosed herein. The exemplary mouth guard was programmed to report an impact event to a nearby wireless server. The server then determined if the impact was severe enough (for example, if the measured acceleration exceeded a predefined threshold) and then the server responded by effecting a change in the color of the light emitted by the LED visual impact indicator. After a certain delay period (determined by the server), the server then effected a change in the color of the light emitted by the LED visual impact indicator back to its original color.

Experimental Example Two

The following experimental example is further described in Birmingham et al., "An Instrumented Mouthguard to Measure Head Accelerations due to Impact," Proceedings of the ASME 2013 Summer Bioengineering Conference (SBC2013), June 26-29, Sunriver, Oreg., USA (2013), which is incorporated by reference herein in its entirety.

It is contemplated that, in the long term, quantitative measurements indicating the magnitude and nature of head impacts can be essential to understanding the biomechanics of head injury. Tools are needed that can quantitatively measure the levels of head acceleration experienced by athletes in a variety of situations in order to assess these risks. The disclosed experiment was aimed at developing instrumentation that is comfortable enough to use in the field and which can repeatably and accurately measure head accelerations from blows to the head. Soccer is a unique sport in that the unprotected head is deliberately used to direct the motion of the ball during play, which makes it practical to study in a controlled laboratory setting. While the possible long-term effects of heading are still subject to debate, there is evidence which suggests that it is responsible for transient neurocognitive deficits and transient concussion symptoms. The work presented here demonstrates the use of six 1-axis accelerometers, which make the mouthguard more slim and comfortable while allowing both linear and angular accelerations of the head to be determined.

The subject of this research was a 25-year-old male soccer player in good physical condition, with a height of 183 cm and a mass of 92 kg. A custom thermoplastic mouthguard, pictured in FIG. 7, was created from an impression of the subject's teeth and instrumented with six 1-axis microelectromechanical system (MEMS) accelerometers (Analog Devices, ADXL001), capable of measuring large accelerations with high acquisition rates (±70 g, 30 kHz), but of small enough mass to avoid significant inertial effects on the player's head.

The mouthguard was connected to a microcontroller, which wirelessly sent data to a data logger and laptop computer. During experimentation, a soccer ball launching machine (Sports Soccer Machine M1800, Jugs Sports Equipment) was used to launch balls at the test subject at speeds up to approximately 12 m/s. A standard size 5 soccer ball with diameter 22-23 cm, mass 0.43 kg, inflated to 62 kPa, was used. Experiments were performed indoors to eliminate wind. Each heading event was recorded using a high speed (HS) camera (HotShot 512 INT, NAC Image Technology) capable of recording up to 2,000 fps at its full resolution of 512×512 pixels. Contact between the ball and head typically lasts tens of milliseconds, allowing between 20 and 30 frames to be captured over the course of the impact. Frame-by-frame analysis of each video was performed using the Image Processing Toolbox available with MATLAB. The position of the ball was determined in each frame, as well as its geometric deformation during contact with the head. The pre- and post-impact velocities and the impulse delivered by the ball to the head were calculated from this information. The position of the head was tracked frame-by-frame just prior to impact, allowing the pre-impact head velocity to be determined. For lower initial ball velocities, where head velocity was appreciable, the relative impact speed between the ball and head was estimated by adding the incoming ball velocity with the pre-impact head velocity.

Figure 10:
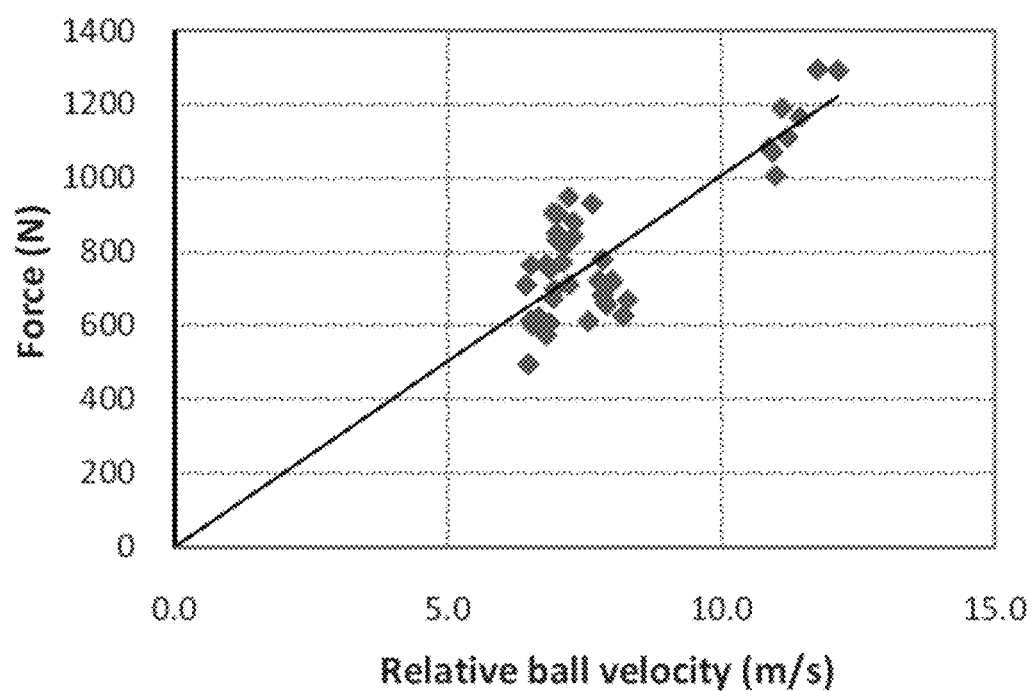
FIG. 10 depicts a graph of peak force of a ball on the head of a subject versus the relative ball velocity, as measured by an exemplary mouth guard as disclosed herein.

A total of forty-nine heading events were recorded using the technique described above, at incoming ball speeds between approximately 4 and 12 m/s. The peak force of the ball on the head as a function of relative impact velocity is shown in FIG. 10.

Figure 11:
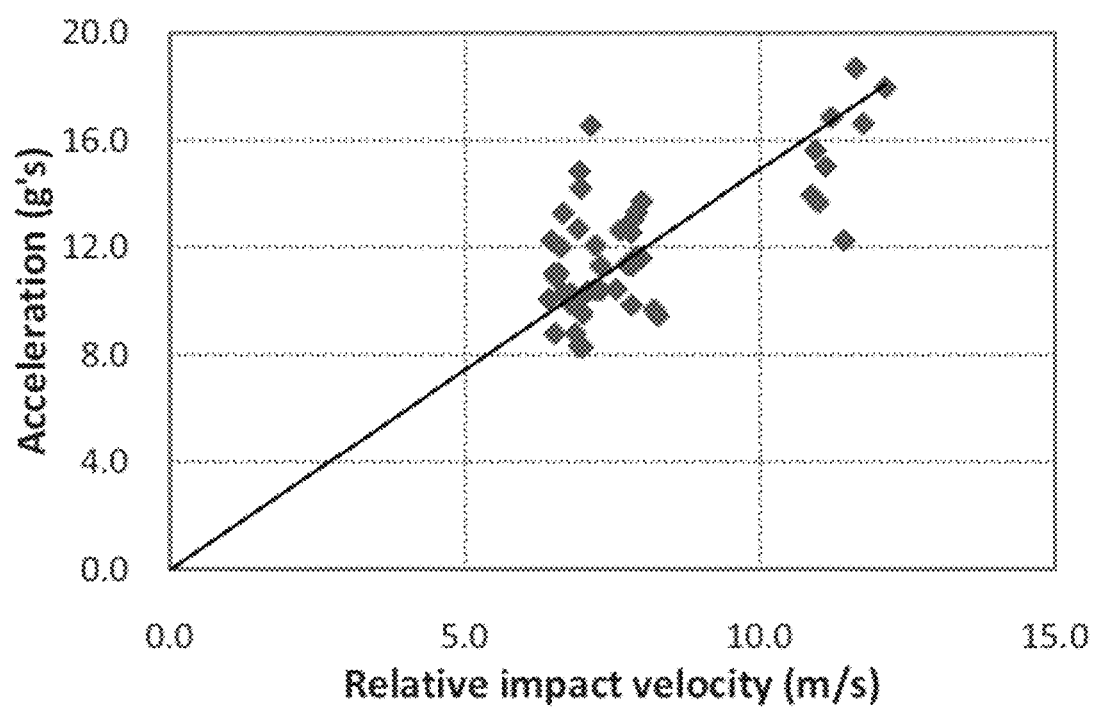
FIG. 11 depicts a graph of the peak magnitude of linear acceleration of the head of a subject in the saggital (xz) plane versus the relative ball velocity, as measured by an exemplary mouth guard as disclosed herein.
Figure 12:
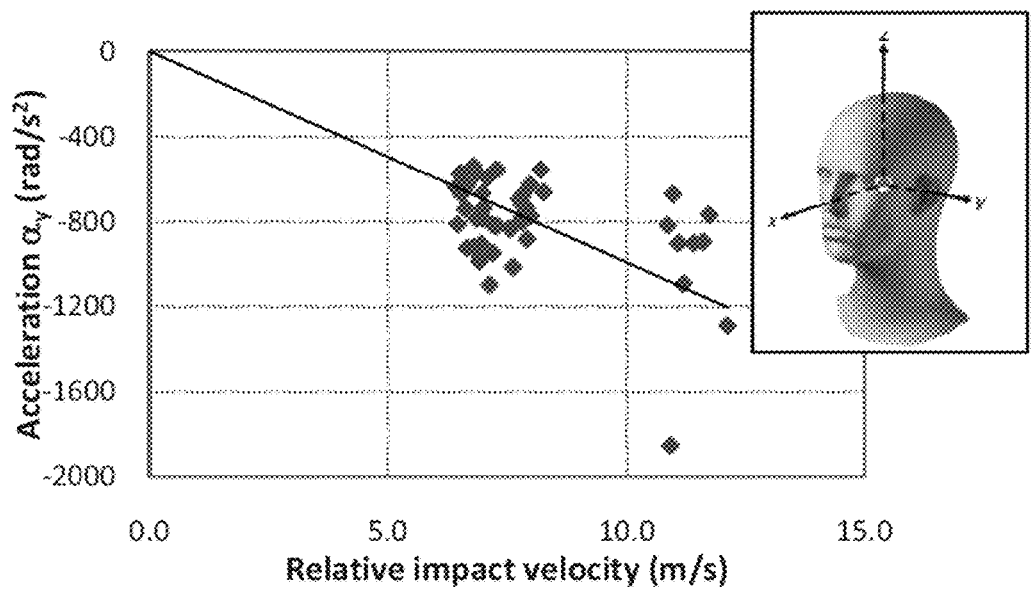
FIG. 12 depicts a graph of the peak angular acceleration of the head of a subject about the y-axis versus the relative ball velocity, as measured by an exemplary mouth guard as disclosed herein.

The linear accelerations measured by the left, right and center accelerometers were transformed to give the linear accelerations of the head CG in the x-, y- and z-directions, and the angular acceleration of the head about the x-, y- and z-axes, using rigid-body mechanics. The center of mass (CG) of the head is assumed to lie at the saggital plane, approximately beneath the zygomatic arch. The peak magnitude of the linear acceleration of the head CG in the saggital (xz) plane is shown in FIG. 11 as a function of relative ball velocity. The coordinate system used to describe the acceleration results is shown in the inset in FIG. 12. Linear acceleration ranged as high as 19 g's for a relative ball velocity of 11.6 m/s. The peak magnitude of the angular accelerations of the head about the y-axis, $\alpha_y$, are shown in FIG. 12. The absolute value of angular acceleration $\alpha_y$ ranged as high as 1852 rad/s$^2$ for a relative ball velocity of 10.9 m/s. Angular velocities about the x- and z-axes, $\alpha_x$ and $\alpha_z$, were generally not appreciable for the headers recorded during this experiment, which has focused frontal headers.

The data presented here suggest a linear relationship between pre-impact velocity and delivered force, maximum linear acceleration of the head, and maximum angular acceleration of the head $\alpha_y$. The results presented here demonstrate successful use of a custom mouthguard instrumented with six 1-axis accelerometers to determine both linear (CG) and angular accelerations of the head during soccer ball heading.

Experimental Example Three

It is contemplated that an exemplary wireless instrumented mouth guard as disclosed herein can be evaluated using standard methods provided by the National Operating Committee on Standards for Athletic Equipment (NOCSAE). The mouth guard can be instrumented with six 1-axis accelerometers to measure the accelerations of the head during an impact event. Traumatic brain injury (TBI) and mild traumatic brain injury (mTBI) are increasingly seen as an important public health issue, although current methods of detecting and diagnosing cases of TBI and mTBI leave much room for improvement. It is contemplated that the disclosed mouth guards can be adopted in the field as both a research tool and a safety device for measuring accelerations of the head during impact. It is further contemplated that the spatially-separated accelerometers of the mouth guard can allow the linear and angular accelerations to be calculated at the head center of gravity (CG). It is further contemplated that the wireless transmitter of the mouth guard can allow the wearer to move freely and without being tethered to a large data acquisition unit. It is still further contemplated that the disclosed mouth guard can provide the greatest level of fit and protection available.

It is contemplated that an anthropomorphic testing dummy (ATD) headform with embedded accelerometers capable of directly measuring the accelerations of the headform CG can be used to verify the efficacy of the instrumented mouth guard to determine the accelerations of the head CG. The headform can also allow the study of impact speeds and directions that cannot be tested in a laboratory setting with live human subjects. Specifically, a NOCSAE standard headform and a NOCSAE standard drop test can be used. It is contemplated that this equipment and method can allow for the standardized testing to verify and characterize the design of the prototype, including the reliability of the prototype during severe and repeated impacts. This is a necessary step in technology transfer of the instrumented mouth guard from the laboratory to the field and to commercialization.

It is contemplated that an evaluation of the performance of a mouthguard instrumented with six 1-axis accelerometers to measure the accelerations of the head during an impact event can be conducted. This work can be conducted using standards provided by the National Operating Committee on Standards for Athletic Equipment (NOCSAE). This is a necessary step in technology transfer of the instrumented mouthguard from the laboratory to the field and to commercialization.

Traumatic brain injury (TBI) and mild traumatic brain injury (mTBI) are increasingly seen as an important public health issue, especially for active duty military. Current methods of detecting and diagnosing cases of TBI and mTBI leave much room for improvement. The military mainly relies on self-reporting after the fact and uses a battery of neurocognitive assessment tools to confirm diagnosis, which are unfortunately susceptible to confounding variables that can lead to false positives. Meanwhile, athletic coaches and physicians rely on detecting neurocognitive symptoms on the sidelines based on guidelines that lack empirical basis but at the same time are the best available. Neurocognitive symptoms arise as the result of TBI, but head trauma is ultimately the result of applied forces which result in accelerations that can be measured. A combined approach of instrumentation technology and neuroscience is needed to truly make progress towards detecting and treating instances of probable TBI. It is contemplated that the mouth guard and systems disclosed herein can be configured to detect instances of probable TBI in a quantitative manner.

Figure 13:
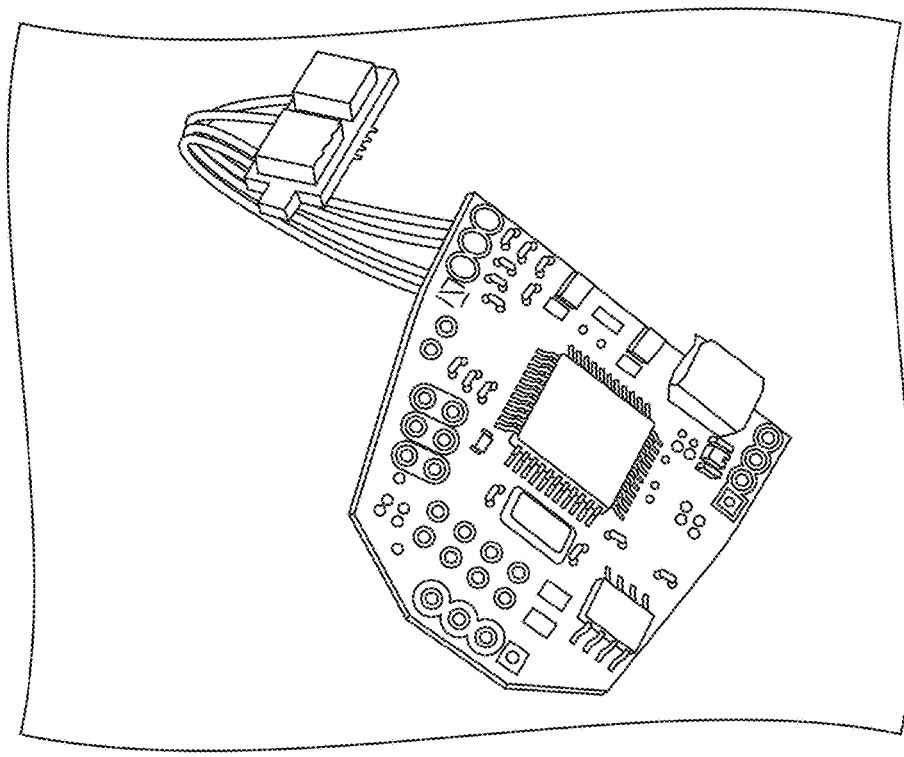
FIG. 13 is an image of an exemplary microcontroller with a wireless transmitter and an accelerometer board as disclosed herein.

The exemplary device relies on three groups of two 1-axis accelerometers arranged at left, right and center locations on a custom mouth guard (see FIG. 7). A microprocessor board can collect and store the data and wirelessly transmits the data to a portable laptop computer (FIG. 13). The microprocessor board can be positioned in the mouth guard in the roof of the mouth. A battery and charging circuit can be positioned in the cheek of the mouth guard, forward of the accelerometers. All of the electronics can be included in the mouth guard, and it can be truly wireless. Thus, the subject can be untethered, which is essential for a practical device that may one day be adopted in the field. The spatial arrangement of the accelerometers around the upper jaw can allow both linear and angular accelerations of the head center of gravity (CG) to be determined. It is contemplated that both linear and angular accelerations can contribute to the damage associated with head trauma. The disclosed custom mouth guard can provide a rigid connection with skull, allowing accelerations of the head to be measured through the rigid connection of the molars to the skull, unlike devices that are meant to be strapped to the head or devices that feature accelerometers mounted in helmets. In addition, it is contemplated that custom mouth guards can offer the best fit and protection to athletes and are a better option for this type of device than mouth formed, or "boil and bite" mouth guards. Other existing mouth guards are not wireless, can only measure linear accelerations, and/or are "boil and bite" mouth guards.

It is contemplated that an anthropomorphic testing dummy (ATD) headform with embedded accelerometers can provide a direct measurement of the CG acceleration values for comparison with those determined using the instrumented mouth guard. It is contemplated that rigid-body mechanics can be used to transform linear accelerations measured by the left, right and center accelerometers to determine the linear and angular accelerations of the head CG in the x-, y- and z-directions. The use of an anthropomorphic testing dummy (ATD) headform with embedded accelerometers capable of directly measuring the accelerations of the headform CG can allow for verification of the efficacy of the instrumented mouthguard in determining the accelerations of the head CG. The headform can also allow the study of impact speeds and directions that could not be tested in a laboratory setting with live human subjects. This equipment and method can allow for the standardized testing to verify and characterize the design of the mouth guard, including the reliability of the mouth guard during severe and repeated impacts. It is contemplated that this is a necessary step in technology transfer of the instrumented mouth guard from the laboratory to the field and to commercialization.

The National Operating Committee on Standards for Athletic Equipment (NOCSAE) has developed numerous standard performance specifications for a variety of athletic gear, and also standard tests and tools by which performance standard verification and research into topics of concern for athletic safety might be conducted. One of these tools is the NOCSAE standard headform, developed to accurately approach human cadaver head response to impact, and which features bone structure, a silicon gel brain, and silicon rubber skin. The NOCSAE standard headform does not include either an upper or lower jaw, but it is contemplated that the headform can be modified to accept the custom mouth guard by rigid attachment of a set of molded teeth. Another standard tool for investigations into athletic safety developed by NOCSAE is its standard drop test, in which an instrumented headform (often fitted with a helmet) is dropped from various heights onto a modular elastomer programmer (MEP) pad on an anvil. The headform can be mounted on a carriage and guide assembly to ensure impact location.

It is contemplated that a complete drop tower and other equipment can be used to perform the NOCSAE standard drop test. It is contemplated that a NOCSAE standard headfrom can be modified for operative coupling to a mouth guard as disclosed herein. It is further contemplated that numerous iterations of the NOCSAE standard drop test can be performed at various speeds and head locations. Embedded accelerometers within the headform can directly measure the acceleration at the headform CG, which can be compared with values of headform CG acceleration calculated using the accelerations measured by the accelerometers in the mouth guard. It is contemplated that the directly determined and calculated values of headform CG acceleration can show good agreement. Further, it is contemplated that the relationship between relative impact velocity and peak acceleration can be linear. Additional results that have not previously been possible can be collected, including results from impacts at relatively high speeds and results from impacts at various locations around the head.

Experimental Example Four

An exemplary helmet/mouth guard system as disclosed herein was evaluated. Head trauma and its attendant symptoms are increasingly recognized as a serious public health concern, with active-duty military and athletes particularly at risk. It is contemplated that the exemplary helmet/mouth guard system can be uniquely practical for collecting data on head trauma in the field. It is contemplated that having instrumentation in the mouth guard rather than the helmet can allow accelerations of the head and intraoral biometrics to be measured directly, and moving the remaining electronics out of mouth guard and into helmet can result in a device comfortable enough to be worn routinely. The exemplary system places only the accelerometers, electrodes, and sensors in the mouth guard; it is contemplated that all other electronics, including microcontroller, memory, transmitter, charging circuit and battery, can be placed in the helmet.

Head trauma and its attendant symptoms are increasingly recognized as a serious public health concern. Groups who are particularly at risk for repeated head injury include active-duty military and athletes at the professional, college and youth levels. The most troubling symptoms of concussive injury (particularly repeated concussive injury) include disruptions in normal neurocognitive function, which unfortunately are difficult to measure quantitatively at the time of injury. Instrumentation is clearly needed to quantitatively measure the severity of concussive injuries as they occur in the field. Furthermore, because head trauma is a sudden and unexpected event, it is contemplated that such instrumentation should be in the form of a device comfortable enough to be worn routinely. In order to be adopted widely enough to collect the large amounts of data needed to examine head trauma on a large scale, it is contemplated that the instrumentation should be capable of measuring, recording and transmitting the data required and provide sufficient ergonomic comfort to be worn by at-risk populations at all times, including in situations where there would ideally be no trauma. It is contemplated that an ergonomic wireless instrumented helmet/mouthguard system can be evaluated in view of these goals.

Currently, diagnosis of traumatic brain injury (TBI) and mild traumatic brain injury (mTBI) takes place post-trauma and is reflective, anecdotal and/or observational. Among deployed troops, self-report is the primary means of screening for probable TBI and mTBI, with a battery of neurocognitive assessment tools needed to confirm diagnosis. These tools have limitations, including susceptibility to confounding variables that can lead to false positives. Milder injuries that do not result in loss of consciousness (LOC) are particularly hard to diagnose because they usually occur away from the presence of medical professionals who can recognize the signs of altered consciousness. For athletes, the severity of injury is generally assessed on the sidelines by physicians, athletic trainers and/or coaches using a set of accepted guidelines such as those published by the American Academy of Neurology. These guidelines were developed using consensus clinical judgment and do not have empirical basis, but continue to be used in the absence of anything more concrete.

Existing instrumentation for directly measuring the accelerations of the head due to impacts to the head were designed to be used in a research setting and may not translate well to the field. Research into a practical means for measuring head accelerations in the field has to date focused on measuring helmet accelerations. However, the accelerations experienced by the head itself are quite different from those experienced by the helmet. Because of these differences, previous work measuring helmet acceleration has emphasized correlation between helmet acceleration and the incidence of concussion instead of using helmet acceleration data to make direct, quantitative predictions of head accelerations.

Rather than using an accelerometer-instrumented helmet to collect data that can only be used correlatively, the disclosed custom mouth guard can be attached to a helmet by a tether. The disclosed device is similar to the helmets with tethered mouth guards already mandated in many contact sports. In fact, the US National Collegiate Athletic Association currently requires mouth guards for four sports (American football, ice hockey, lacrosse and field hockey), and the American Dental Association recommends mouth guards in 29 sports and exercise activities. It is contemplated that a custom mouth guard molded to the upper teeth provides a rigid connection to the skull and is an effective means for directly measuring accelerations to the head and intraoral biometrics. It is further contemplated that the disclosed mouth guard/helmet system can provide a tool that is uniquely practical for collecting data on head trauma in the field. It is contemplated that having accelerometers, electrodes, and sensors in a mouth guard rather than a helmet can allow accelerations of the head and intraoral biometrics to be measured directly, and moving the remaining electronics (including the microprocessor, memory, wireless transmitter, charging circuit and battery) out of mouth guard and into helmet can result in a device comfortable enough to be considered ergonomic and worn routinely. A major barrier to the creation of an instrument like the disclosed device has been the lack of commercially-available sensor components capable of performing the measurements required. It is only within approximately the past two years that accelerometers capable of measuring the large accelerations seen in this application have become commercially available in packages small enough to fit inside the human mouth. Due to recent advances in MEMS accelerometers, the size of high bandwidth high-g accelerometers has been reduced to less than 0.09 cm$^3$ per measurement axis. This volume, which can be spatially distributed around the upper jaw, allows for incorporation of high-performance accelerometer devices into the mouth guard. It is contemplated that the spatial separation of six 1-axis accelerometers (placed orthogonally in groups of two) within the mouth guard can allow both the linear and angular accelerations of the head to be measured during an impact event (see FIG. 7).

In order for the raw linear accelerations given by the accelerometers in the left, right and center of the mouth guard to be translated into the linear and rotational accelerations of the head center of gravity (CG), it is contemplated that the three groups of 1-axis accelerometers can be placed orthogonally. It is contemplated that this can be accomplished by using SolidWorks or other appropriate modeling software to design a bridge (see, e.g., FIG. 4), which can be constructed of ABS plastic with a 3D printer (see, e.g., FIG. 5).

It is contemplated that the disclosed mouth guard can be readily manufactured utilizing the current state-of the art in fabrication of athletic mouth guards. It is further contemplated that custom mouth guards offer the greatest protection from injury. In exemplary aspects, it is contemplated that the mouth guard can comprise ethylene vinyl acetate (EVA). For example, the mouth guard can optionally comprise a composite structure with layers of more rigid EVA surrounding a core of more compliant EVA. It is contemplated that a mouth guard of the kind shown in FIG. 7 can be fabricated using a machine that forms heat-softened sheets of EVA to a mold of the patient's teeth using one of two methods: a vacuum (or suck down) method or a positive pressure method. It is contemplated that the positive pressure method can provide a better fit to the mold. Optionally, it is contemplated that the mouth guard can be formed using bi-lamination by thermo-pressure, which uses the positive pressure method in two stages to laminate separate sheets of EVA together.

Between thermoforming the layers of the mouth guard, it is contemplated that the fabricators can place logos or labels inside the mouth guard. It is further contemplated that the accelerometers and their associated wiring can be placed between layers of formed EVA to create a well-sealed instrumented mouth guard design. In exemplary aspects, only the accelerometers, electrodes, and sensors can be placed in the mouth guard; all other electronics, including microcontroller, memory, transmitter, charging circuit and battery, can be placed in the helmet. The mouth guard can be connected to the helmet via a tether (such as that shown in FIG. 14), which can carry the wires between the accelerometers in the mouth guard and the other electronic components in the helmet.

It is further contemplated that data from the mouth guard can be collected for proof of concept using a human subject. The procedure used in the past for data collection involved launching soccer balls at a subject and asking them to perform a standard heading maneuver such as that found in soccer practice or game play. It is contemplated that such a procedure is not appropriate here because soccer players do not wear helmets. Therefore, it is contemplated that testing of the prototype can occur in the field with a hockey (or other helmeted contact sport) player. A hockey player (or players) can wear the instrumented helmet/mouth guard system during ordinary practice, and the mouth guard can record any events that lead to head accelerations above a certain threshold. The instrumented helmet/mouth guard system can be fitted with an LED or other indicators to notify researchers when these events happen. Acceleration data from the mouth guard can then be downloaded to a computer using the wireless transmitter. The accelerometers in the mouth guard can record local linear accelerations in the x-, y- and z-directions. The spatial positioning of the accelerometers can allow the linear accelerations of the head CG in the x-, y- and z-directions, as well as rotational accelerations of the head about the x-, y- and z-axes, to be calculated. Digital video recordings of the experimental sessions can be made so that it will be clear what events led to what accelerations. It is contemplated that these experimental sessions can demonstrate the potential of the helmet/mouth guard system for adoption in the field.

Exemplary Aspects

In one exemplary aspect, a measurement system for determining at least one physiological condition of a subject is provided. The subject can have a head, a mouth, and upper and lower teeth. The measurement system can comprise a mouth guard and processing circuitry. The mouth guard can comprise a U-shaped element having an outer side wall, an inner side wall, and at least one biting surface, with the outer side wall, the inner side wall, and the at least one biting surface cooperating to define at least one channel configured to receive at least one of the upper teeth and the lower teeth of the subject. The mouth guard can further comprise a plurality of electrodes operatively associated with the U-shaped element, with the plurality of electrodes being spaced from one another about the U-shaped element and configured for contact with a portion of the mouth of the subject. The processing circuitry can be positioned in operative communication with the plurality of electrodes of the mouth guard. The processing circuitry can be configured to measure the impedance between respective electrodes of the plurality of electrodes. The measured impedance between respective electrodes of the plurality of electrodes can be indicative of the at least one physiological condition of the subject.

In another exemplary aspect, the plurality of electrodes can comprise at least three electrodes.

In another exemplary aspect, the mouth guard can further comprise a plurality of temperature sensors in operative communication with the processing circuitry, with each temperature sensor of the plurality of temperature sensors being configured to produce a temperature signal indicative of the temperature within the mouth of the subject, and with each temperature sensor of the plurality of temperature sensors being configured to transmit its temperature signal to the processing circuitry.

In another exemplary aspect, the mouth guard can further comprise a plurality of heart rate sensors in operative communication with the processing circuitry, with each heart rate sensor of the plurality of heart rate sensors being configured to produce a heart rate signal indicative of the heart rate of the subject, and with each heart rate sensor of the plurality of heart rate sensors being configured to transmit its heart rate signal to the processing circuitry.

In another exemplary aspect, the mouth guard can further comprise a plurality of blood pressure sensors in operative communication with the processing circuitry, with each blood pressure sensor of the plurality of blood pressure sensors being configured to produce a blood pressure signal indicative of the blood pressure of the subject, and with each blood pressure sensor of the plurality of blood pressure sensors being configured to transmit its blood pressure signal to the processing circuitry.

In another exemplary aspect, the processing circuitry can comprise a microcontroller.

In another exemplary aspect, the mouth guard can further comprise means for generating an alarm, and the means for generating the alarm can be in operative communication with the microcontroller.

In another exemplary aspect, the means for generating an alarm can comprise at least one light-emitting diode (LED), and each LED of the at least one LED can be configured to emit light of a predetermined color in response to an alarm condition.

In another exemplary aspect, the processing circuitry can comprise a memory configured to store the impedance measurements.

In another exemplary aspect, the mouth guard can further comprise a plurality of accelerometers operatively associated with the U-shaped element, with the plurality of accelerometers being spaced from one another about the U-shaped element, each accelerometer of the plurality of accelerometers being configured to produce an output indicative of the linear and angular acceleration of the mouth guard, and the processing circuitry being configured to receive the outputs from the plurality of accelerometers.

In another exemplary aspect, the processing circuitry can be configured to determine the severity of a head impact experienced by the subject based upon the measured impedance within the mouth of the subject and the linear and angular acceleration of the mouth guard.

In another exemplary aspect, the processing circuitry can be configured to determine the severity of a head impact experienced by the subject based upon the linear and angular acceleration of the mouth guard and at least one of the measured impedance within the mouth of the subject, the temperature of the subject, the blood pressure of the subject, and the heart rate of the subject.

In another exemplary aspect, the processing circuitry is configured to identify at least one alarm condition based upon at least one of the recorded impedance measurements, the temperature signals, the blood pressure signals, the heart rate signals, and the outputs of the accelerometers.

In one exemplary aspect, a measurement system for determining at least one physiological condition of a subject is disclosed. The subject can have a head, a mouth, and upper and lower teeth. The measurement system can comprise a mouth guard, a helmet, a strap, and processing circuitry. The mouth guard can comprise a U-shaped element having an outer side wall, an inner side wall, and at least one biting surface, with the outer side wall, the inner side wall, and the at least one biting surface cooperating to define at least one channel configured to receive at least one of the upper teeth and the lower teeth of the subject. The mouth guard can further comprise a plurality of measurement assemblies operatively associated with the U-shaped element, with the plurality of measurement assemblies being spaced from one another about the U-shaped element and configured for contact with a portion of the mouth of the subject, with each measurement assembly being configured to produce at least one output indicative of the at least one physiological condition of the subject. The strap can be coupled to and extend between the mouth guard and the helmet. The processing circuitry can be positioned in operative communication with the plurality of measurement assemblies and be configured to receive the at least one output from the plurality of measurement assemblies. The processing circuitry can be positioned at least partially within the helmet. The strap can comprise at least one wire positioned in electrical communication with the plurality of measurement assemblies and the processing circuitry.

In another exemplary aspect, the plurality of measurement assemblies can comprise at least one of: a plurality of electrodes; a plurality of accelerometers; a plurality of temperature sensors; a plurality of blood pressure sensors; and a plurality of heart rate sensors.

In another exemplary aspect, the plurality of measurement assemblies can comprise a plurality of accelerometers operatively associated with the U-shaped element, with the plurality of accelerometers being spaced from one another about the U-shaped element, each accelerometer of the plurality of accelerometers being configured to produce an output indicative of the linear and angular acceleration of the mouth guard, the processing circuitry being configured to receive the outputs from the plurality of accelerometers, and the processing circuitry being configured to determine the severity of a head impact experienced by the subject based upon the linear and angular acceleration of the mouth guard.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A measurement system for determining at least one physiological condition of a subject, the subject having a head, a mouth, and upper and lower teeth, the measurement system comprising:
   a mouth guard comprising: a U-shaped element having an outer side wall, an inner side wall, and at least one biting surface, the outer side wall, the inner side wall, and the at least one biting surface together defining at least one channel configured to receive at least one of the upper teeth and the lower teeth of the subject;
   a plurality of electrodes operatively associated with the U-shaped element, the plurality of electrodes being spaced from one another about the U-shaped element and configured to remain in contact with tissue of the mouth of the subject when the at least one channel of the mouth guard receives at least one of the upper teeth and the lower teeth of the subject; and
   processing circuitry in operative communication with the plurality of electrodes of the mouth guard,
   wherein the processing circuitry is configured to measure impedance between respective electrodes of the plurality of electrodes through tissue within the mouth of the subject, and
   wherein the processing circuitry is configured to determine at least a respiratory rate of the subject based upon the measured impedance between respective electrodes of the plurality of electrodes, wherein the processing circuitry is configured to:
   (a) record a series of time-separated measurements of impedance within the mouth of the subject;
   (b) calibrate and transform the series of time-separated measurements to identify a plurality of peak impedance measurements within a selected frequency range; and
   (c) use the identified peak impedance measurements to determine the respiratory rate of the subject.

2. The measurement system of claim 1, wherein the plurality of electrodes comprises at least three electrodes.

3. The measurement system of claim 1, wherein the mouth guard further comprises a plurality of temperature sensors in operative communication with the processing circuitry, wherein each temperature sensor of the plurality of temperature sensors is configured to produce a temperature signal indicative of the temperature within the mouth of the subject, and wherein each temperature sensor of the plurality of temperature sensors is configured to transmit its temperature signal to the processing circuitry.

4. The measurement system of claim 1, wherein the mouth guard further comprises a plurality of heart rate sensors in operative communication with the processing circuitry, wherein each heart rate sensor of the plurality of heart rate sensors is configured to produce a heart rate signal indicative of the heart rate of the subject, and wherein each heart rate sensor of the plurality of heart rate sensors is configured to transmit its heart rate signal to the processing circuitry.

5. The measurement system of claim 3, wherein the mouth guard further comprises a plurality of heart rate sensors in operative communication with the processing circuitry, wherein each heart rate sensor of the plurality of heart rate sensors is configured to produce a heart rate signal indicative of the heart rate of the subject, and wherein each heart rate sensor of the plurality of heart rate sensors is configured to transmit its heart rate signal to the processing circuitry.

6. The measurement system of claim 1, wherein the mouth guard further comprises a plurality of blood pressure sensors in operative communication with the processing circuitry, wherein each blood pressure sensor of the plurality of blood pressure sensors is configured to produce a blood pressure signal indicative of the blood pressure of the subject, and wherein each blood pressure sensor of the plurality of blood pressure sensors is configured to transmit its blood pressure signal to the processing circuitry.

7. The measurement system of claim 5, wherein the mouth guard further comprises a plurality of blood pressure sensors in operative communication with the processing circuitry, wherein each blood pressure sensor of the plurality of blood pressure sensors is configured to produce a blood pressure signal indicative of the blood pressure of the subject, and wherein each blood pressure sensor of the plurality of blood pressure sensors is configured to transmit its blood pressure signal to the processing circuitry.

8. The measurement system of claim 1, wherein the processing circuitry comprises a microcontroller.

9. The measurement system of claim 8, wherein the mouth guard further comprises means for generating an alarm, wherein the means for generating the alarm is in operative communication with the microcontroller.

10. The measurement system of claim 9, wherein the means for generating an alarm comprises at least one light-emitting diode (LED), and wherein each LED of the at least one LED is configured to emit light of a predetermined color in response to an alarm condition.

11. The measurement system of claim 1, wherein the processing circuitry comprises a memory configured to store the impedance measurements.

12. The measurement system of claim 1, wherein the mouth guard further comprises a plurality of accelerometers operatively associated with the U-shaped element, the plurality of accelerometers being spaced from one another about the U-shaped element, each accelerometer of the plurality of accelerometers being configured to produce an output indicative of the linear and angular acceleration of the mouth guard, wherein the processing circuitry is configured to:
receive the outputs from the plurality of accelerometers; and
determine a severity of a head impact experienced by the subject based upon the measured impedance within the mouth of the subject and the linear and angular acceleration of the mouth guard.

13. The measurement system of claim 7, wherein the mouth guard further comprises a plurality of accelerometers operatively associated with the U-shaped element, the plurality of accelerometers being spaced from one another about the U-shaped element, each accelerometer of the plurality of accelerometers being configured to produce an output indicative of the linear and angular acceleration of the mouth guard, wherein the processing circuitry is configured to:
receive the outputs from the plurality of accelerometers; and
determine a severity of a head impact experienced by the subject based upon the linear and angular acceleration of the mouth guard and at least one of the measured impedance within the mouth of the subject, the temperature of the subject, the blood pressure of the subject, and the heart rate of the subject.

14. The measurement system of claim 13, wherein the processing circuitry comprises a microcontroller, wherein the mouth guard further comprises means for generating an alarm, the means for generating the alarm being in operative communication with the microcontroller.

15. The measurement system of claim 14, wherein the means for generating the alarm is configured to generate the alarm in response to an alarm condition, and wherein the processing circuitry is configured to identify at least one alarm condition based upon at least one of the recorded impedance measurements, the temperature signals, the blood pressure signals, the heart rate signals, and the outputs of the accelerometers.

16. The measurement system of claim 2, wherein the processing circuitry is configured to determine variations between the impedance of surface tissue and the impedance of bulk tissue within the mouth of the subject.

17. A method for determining at least one physiological condition of a subject, the subject having a head, a mouth, and upper and lower teeth, the method comprising:
positioning a mouth guard within the mouth of the subject, the mouth guard comprising:
a U-shaped element having an outer side wall, an inner side wall, and at least one biting surface, the outer side wall, the inner side wall, and the at least one biting surface together defining at least one channel that receives at least one of the upper teeth and the lower teeth of the subject;
a plurality of electrodes operatively associated with the U-shaped element, the plurality of electrodes being spaced from one another about the U-shaped element and positioned in contact with tissue of the mouth of the subject when the at least one channel of the mouth guard receives at least one of the upper teeth and the lower teeth of the subject;
using processing circuitry in operative communication with the plurality of electrodes of the mouth guard to measure impedance between respective electrodes of the plurality of electrodes through tissue within the mouth of the subject; and
using the processing circuitry to determine a respiratory rate of the subject based upon the measured impedance between respective electrodes of the plurality of electrodes, wherein the processing circuitry is configured to:
(a) record a series of time-separated measurements of impedance within the mouth of the subject;
(b) calibrate and transform the series of time-separated measurements to identify a plurality of peak impedance measurements within a selected frequency range; and
(c) use the identified peak impedance measurements to determine the respiratory rate of the subject.

18. The method of claim 17, wherein the plurality of electrodes comprises at least three electrodes.

19. The measurement system of claim 1, wherein the processing circuitry is configured to transform the series of time-separated measurements using a Fourier transformation.

20. The measurement system of claim 1, wherein the selected frequency range is 0.1 to 1 Hz.

* * * * *